United States Patent
Yeh

(10) Patent No.: US 9,169,509 B2
(45) Date of Patent: Oct. 27, 2015

(54) TOPOISOMERASE 2B AS A PREDICTOR OF SUSCEPTIBILITY TO ANTHRACYCLINE-INDUCED CARDIOTOXICITY

(71) Applicant: Board of Regents, The University of Texas System, Austin, TX (US)

(72) Inventor: Edward T. H. Yeh, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/155,858

(22) Filed: Jan. 15, 2014

(65) Prior Publication Data

US 2014/0200192 A1  Jul. 17, 2014

Related U.S. Application Data

(60) Provisional application No. 61/752,664, filed on Jan. 15, 2013.

(51) Int. Cl.
*A61K 31/704* (2006.01)
*G01N 33/574* (2006.01)
*C12Q 1/533* (2006.01)

(52) U.S. Cl.
CPC .............. *C12Q 1/533* (2013.01); *A61K 31/704* (2013.01)

(58) Field of Classification Search
CPC .................................................... G01N 33/574
USPC .......................................... 435/7.23; 514/34
See application file for complete search history.

(56) References Cited

U.S. PATENT DOCUMENTS

| 7,732,141 B2 | 6/2010 | Kopreski |
| 7,767,390 B2 | 8/2010 | Kopreski |
| 2003/0148345 A1 | 8/2003 | Kopreski |
| 2004/0048279 A1 | 3/2004 | Berlin et al. |
| 2010/0304989 A1 | 12/2010 | Von Hoff et al. |
| 2011/0086765 A1 | 4/2011 | Bertucci et al. |

OTHER PUBLICATIONS

Lyu et al. (Cancer Res 2007, 67(18): 8839-46).*
Division of Internal Medicine News, The University of Texas MD Anderson Cancer Center, Summer 2012 Issue.
Kersting et al., "Topoisomerase II beta expression level correlates with doxorubicin-induced apoptosis in peripheral blood cells", *Naunyn-Schmiedeberg's Arch Pharmacol.*, 374:21-30, 2006.

* cited by examiner

*Primary Examiner* — Yan Xiao
(74) *Attorney, Agent, or Firm* — Parker Highlander PLLC

(57) ABSTRACT

Biomarkers of anthracycline cardiotoxicity are provided. In certain aspects, methods are provided for determining whether a subject will develop cardiotoxicity upon treatment with an anthracycline, such as doxorubicin, by measuring the level of Top2b expression in the subject. In further aspects, methods of a treating a subjects with anthracycline therapeutics and cardioprotective agents are provided.

14 Claims, 21 Drawing Sheets

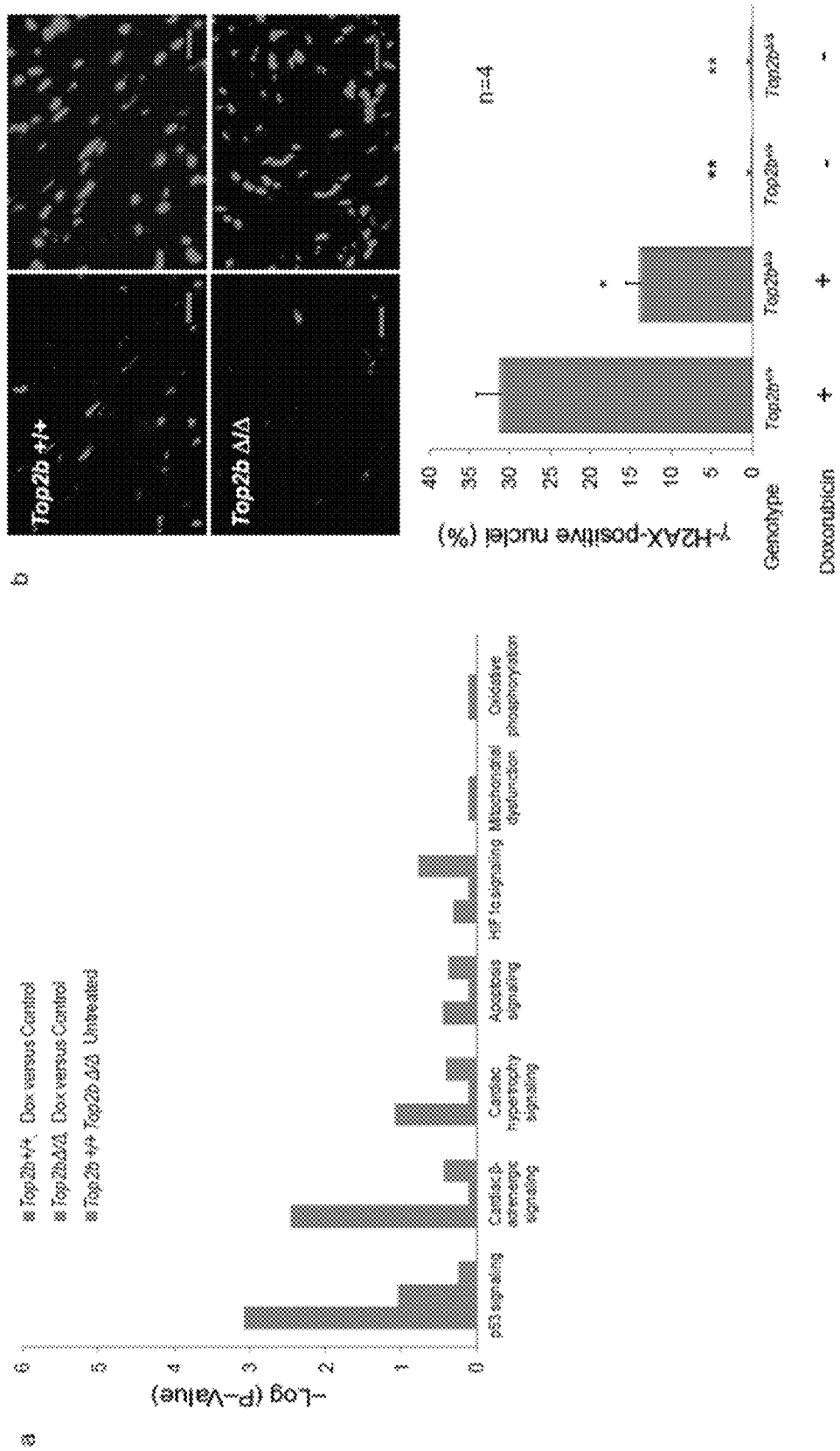
FIG. 1a-b

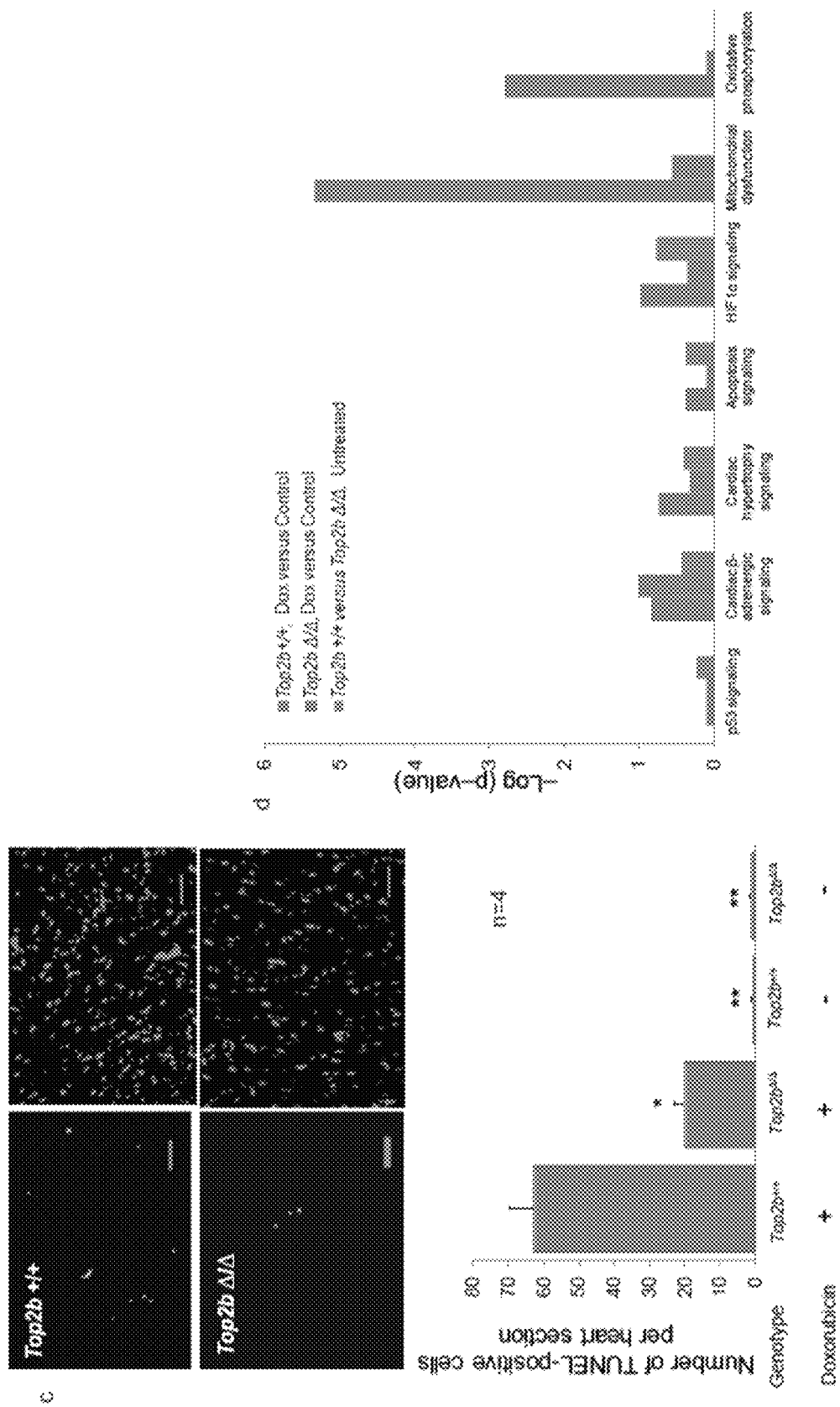
FIG. 1c-d

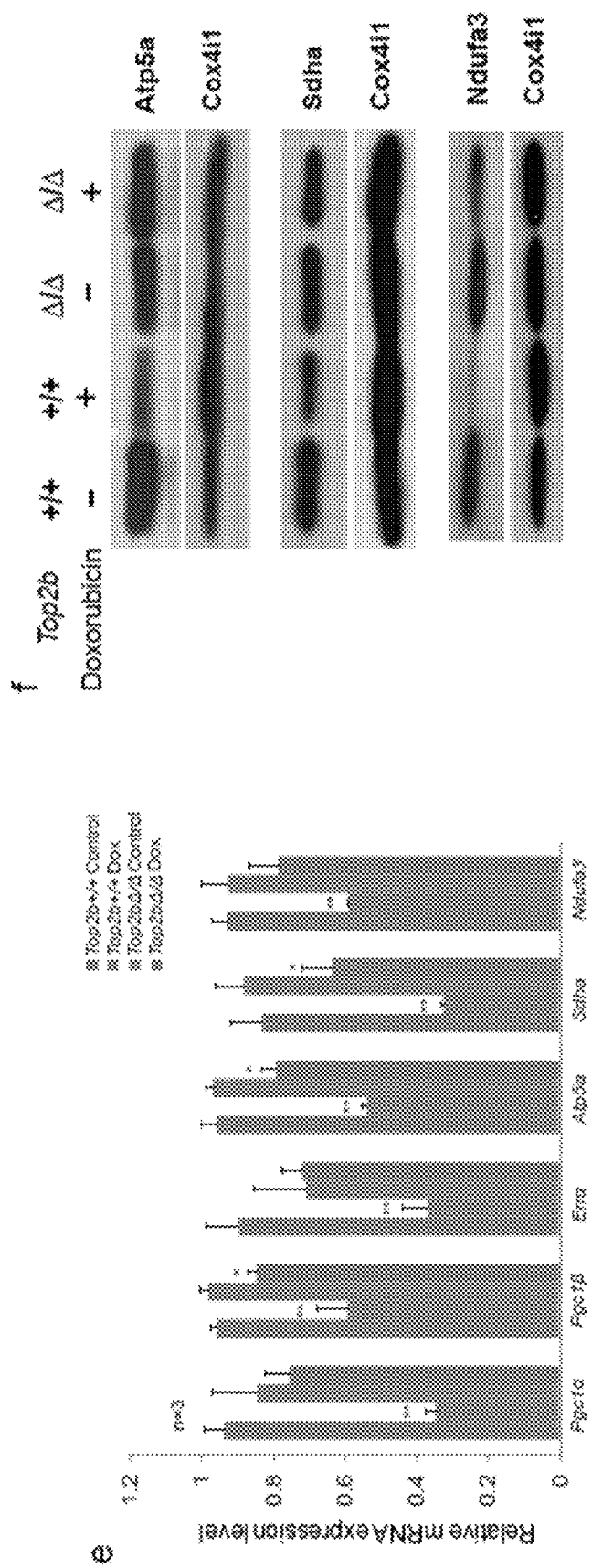
FIG. 1e-f

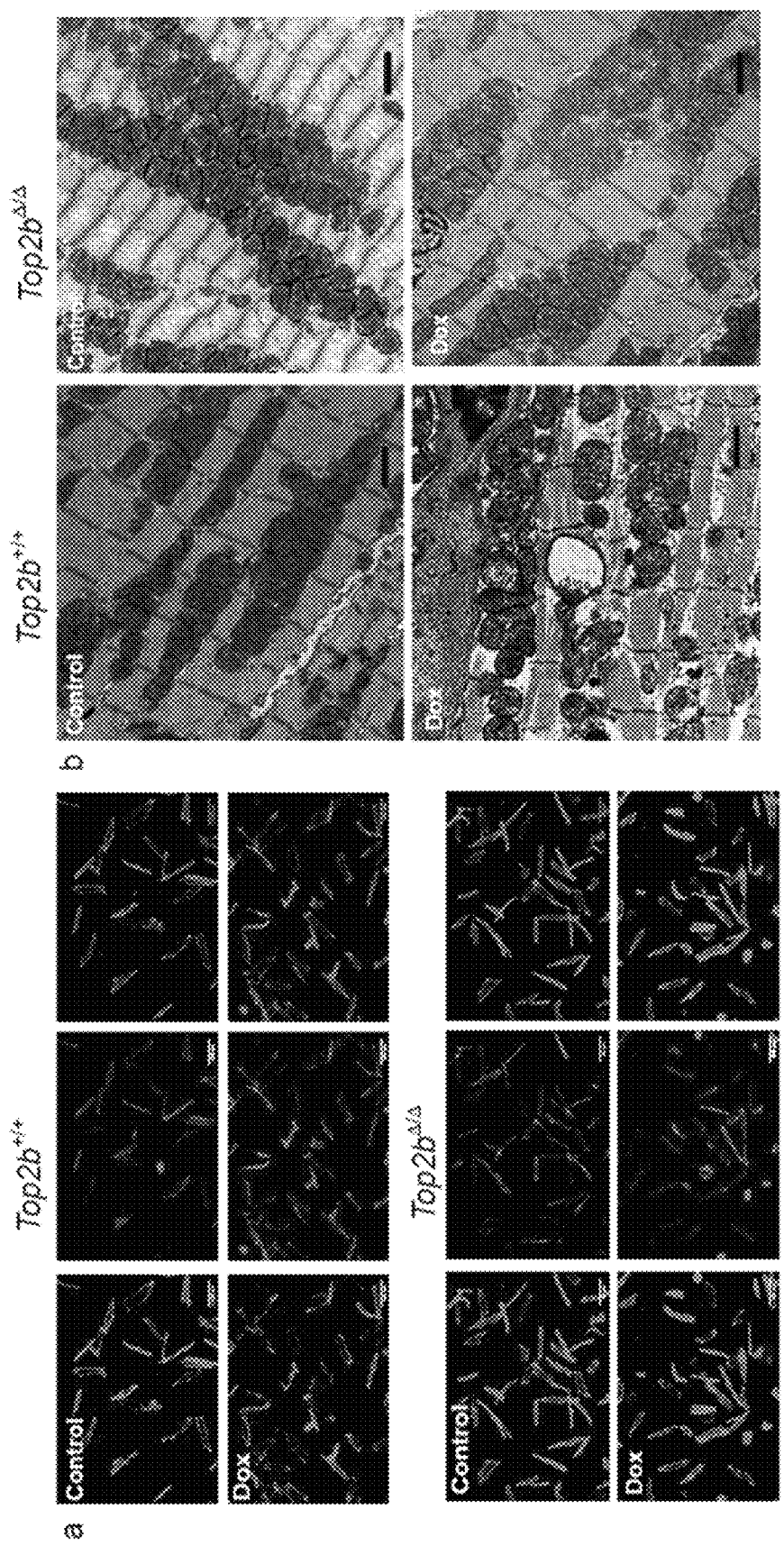
FIG. 2a-b

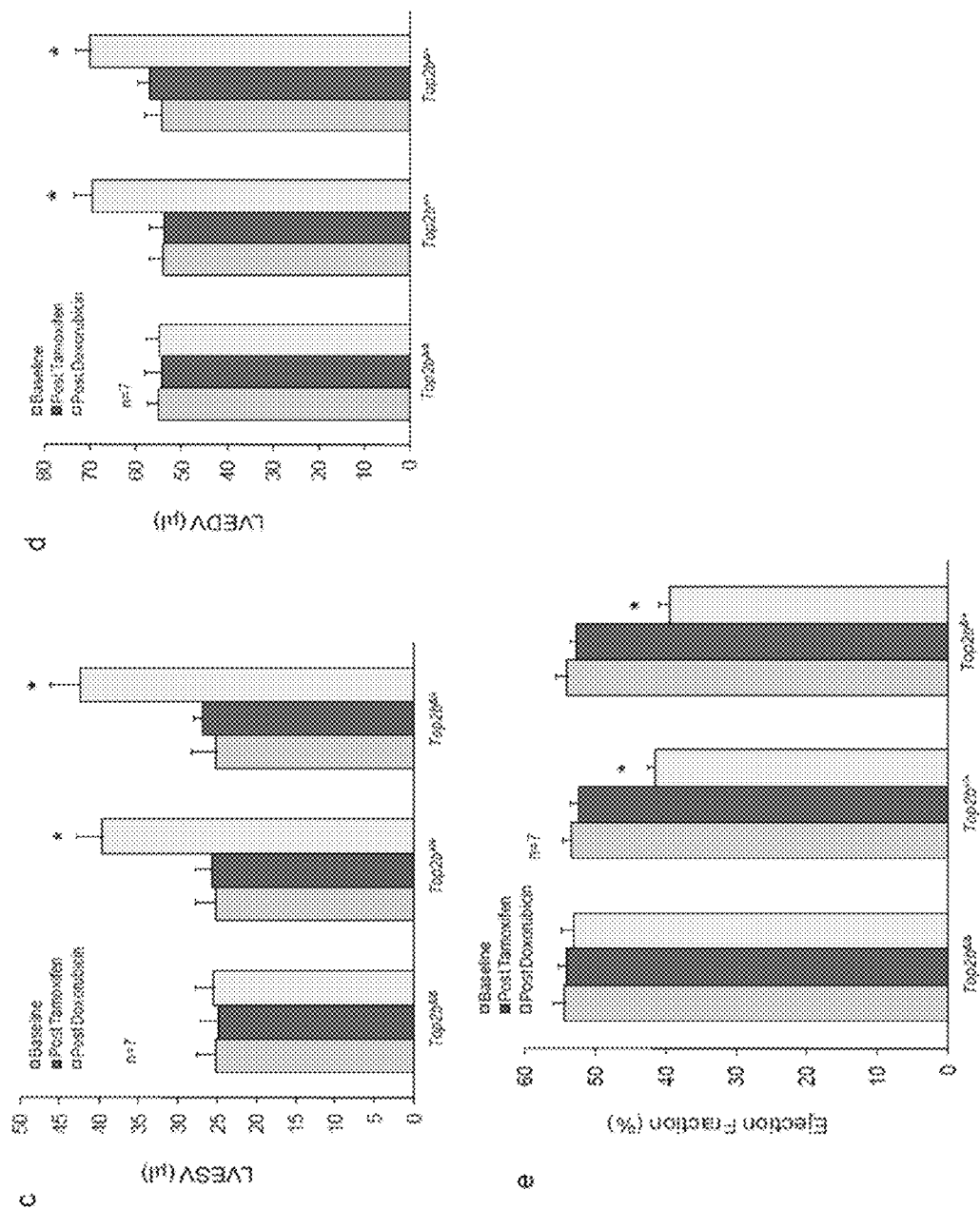
FIG. 2c-e a
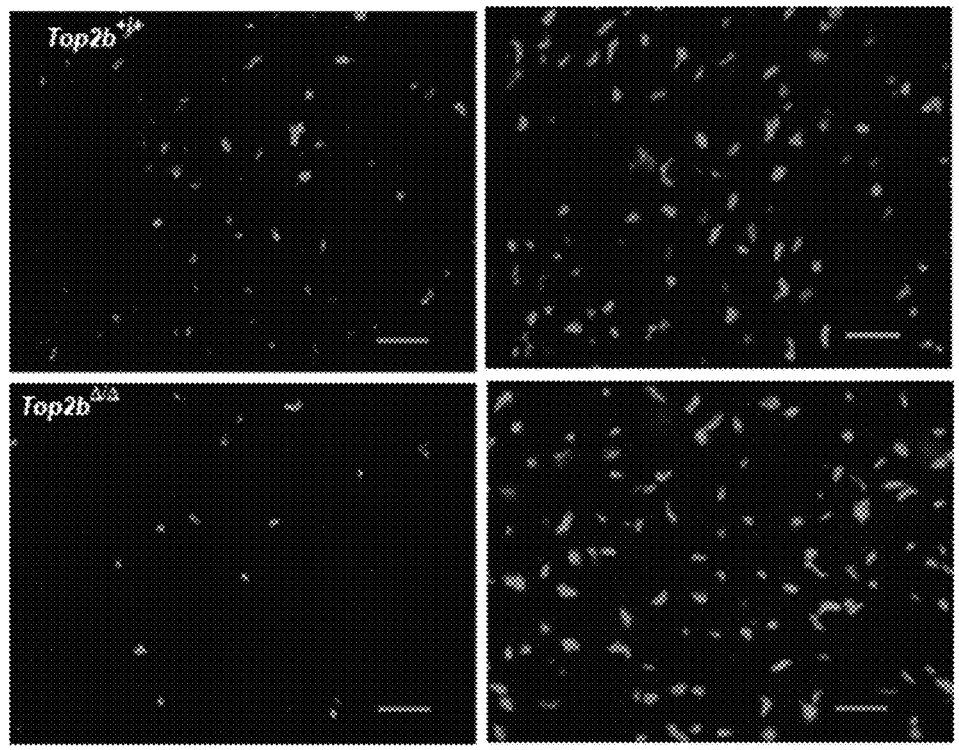
b
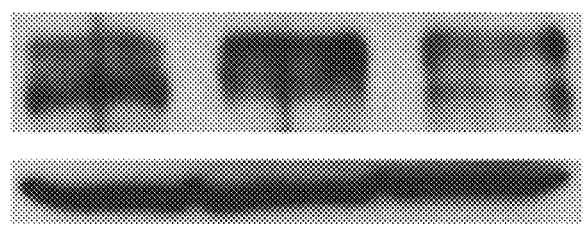
FIG. 3

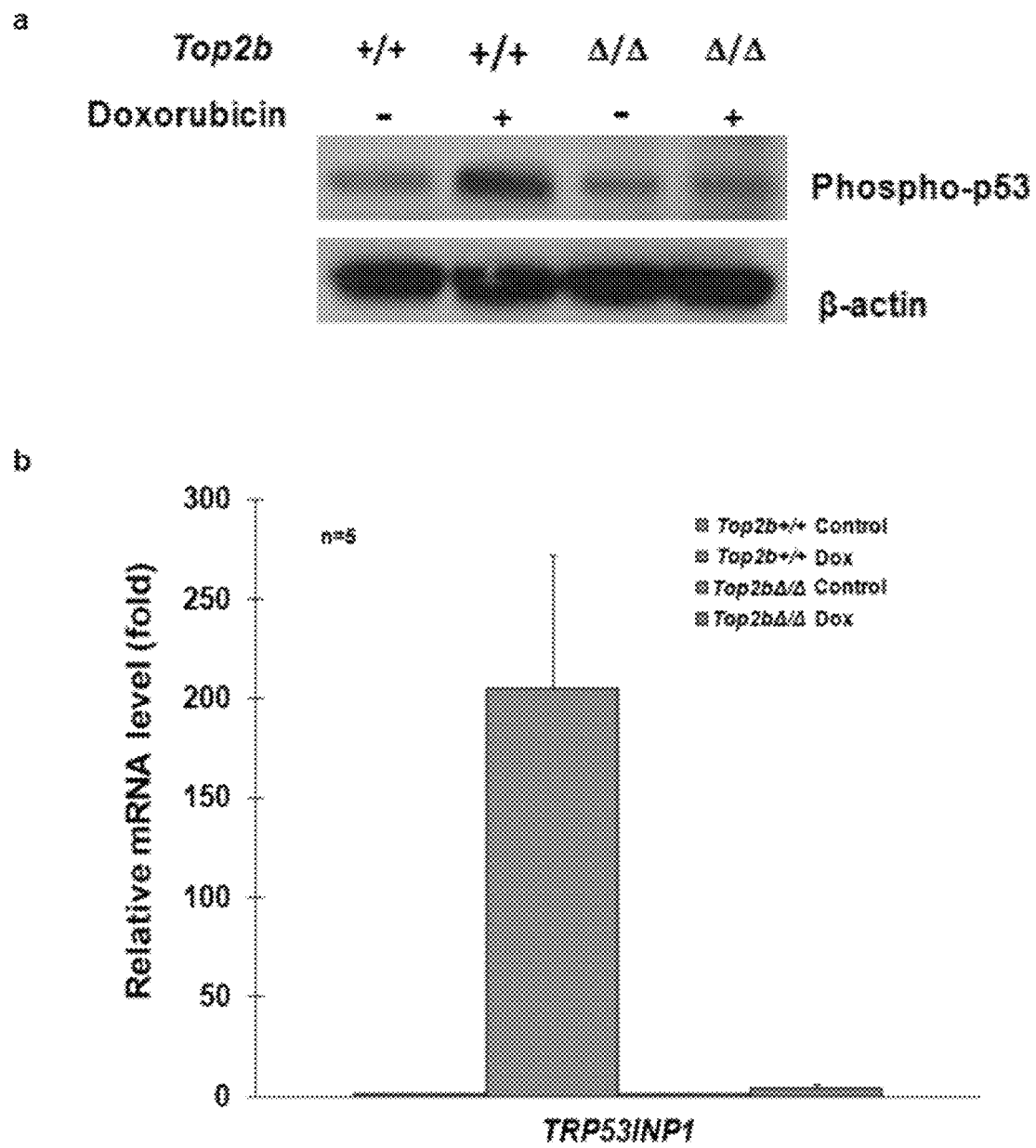
FIG. 4a-b

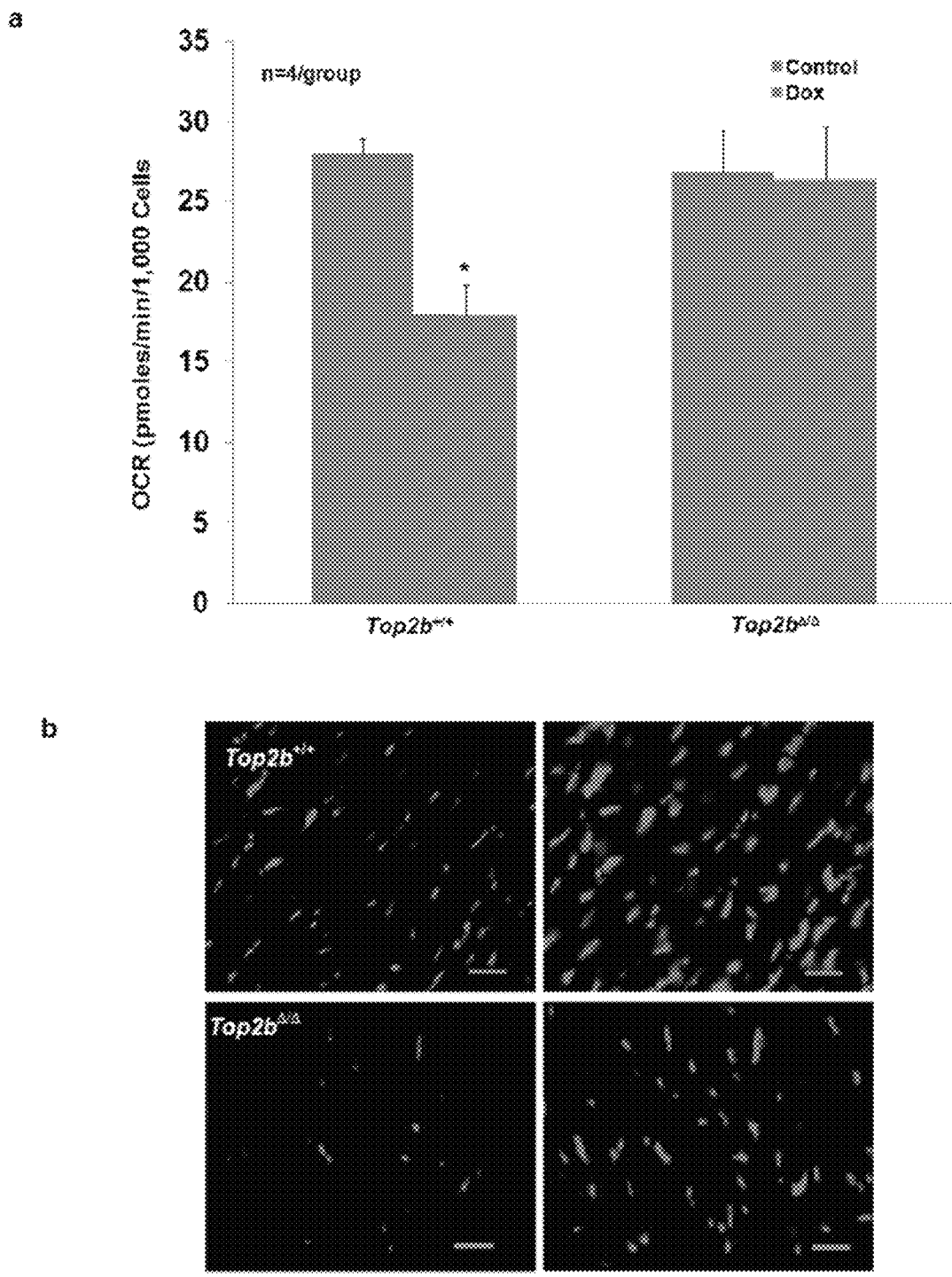
FIG. 5a-b

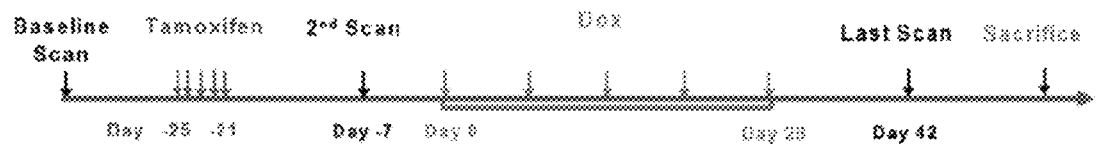
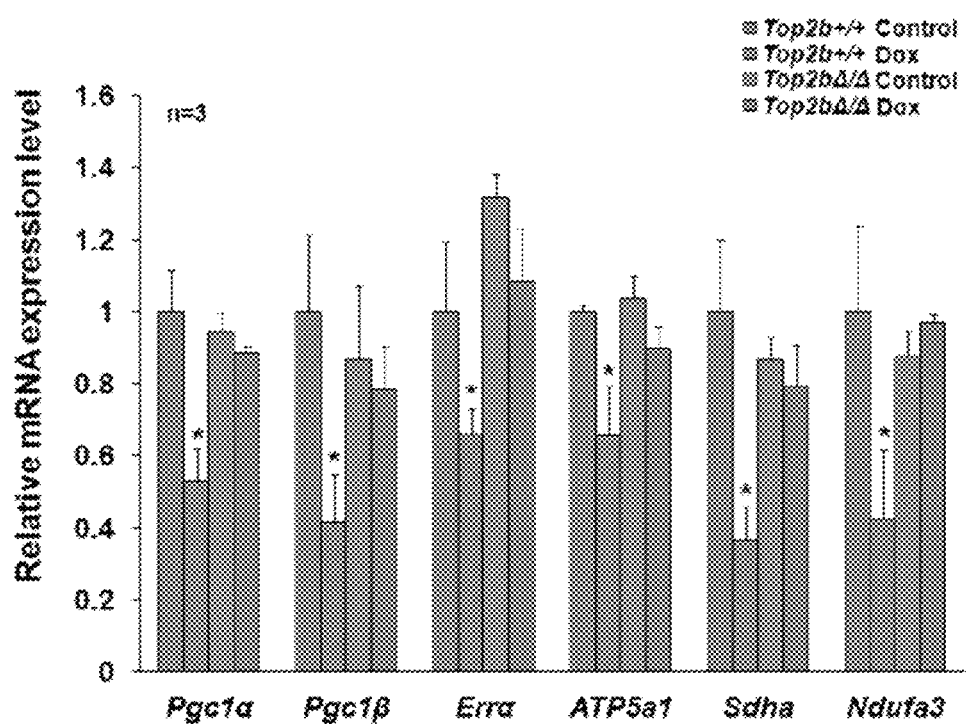
FIG. 6a-b

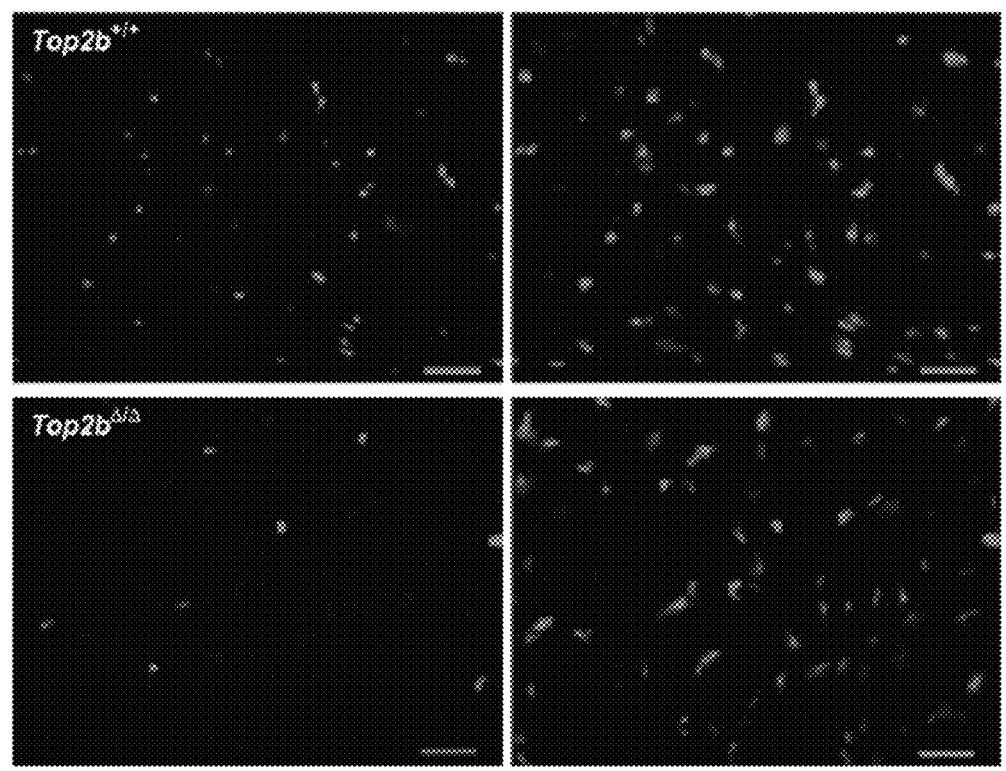
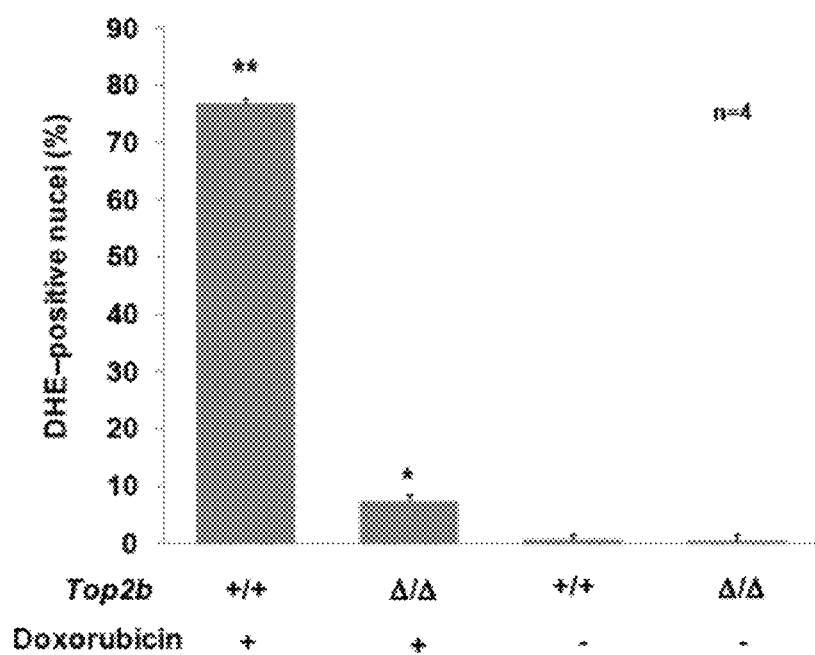
FIG. 6c d
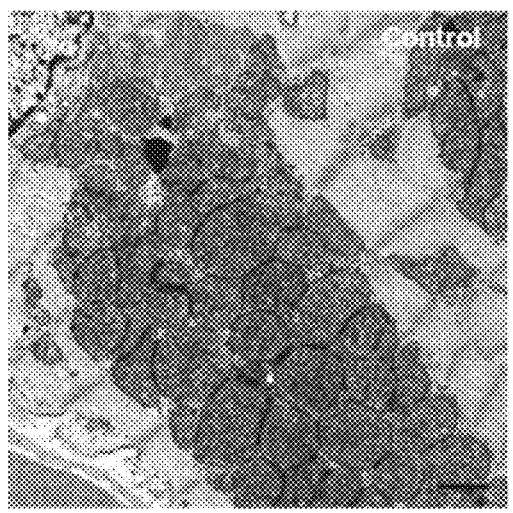 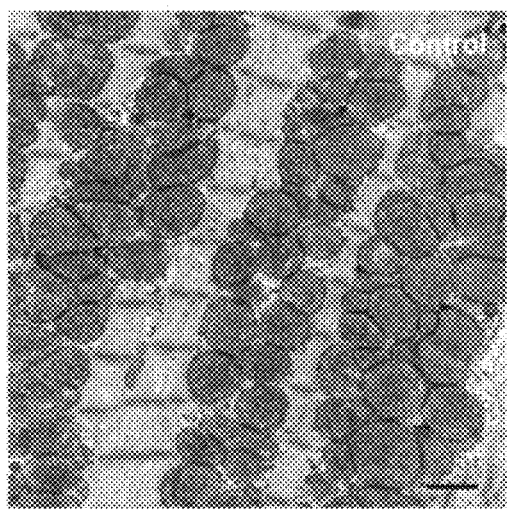
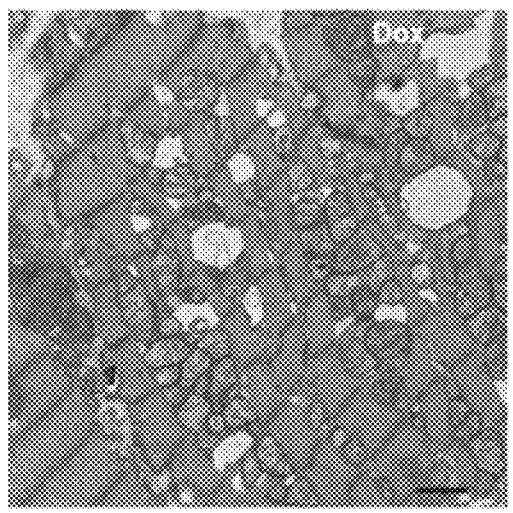 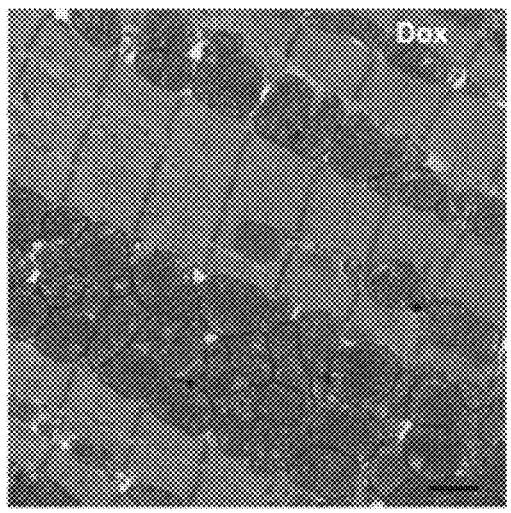
FIG. 6d

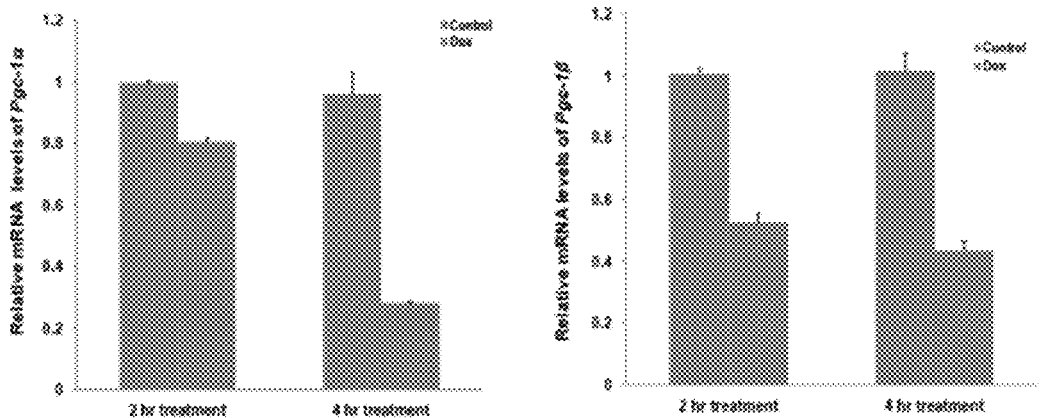
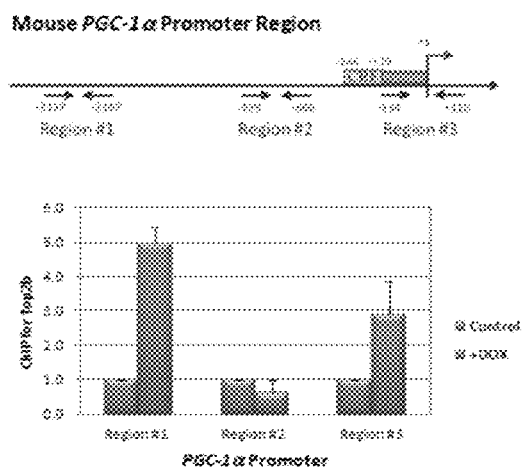
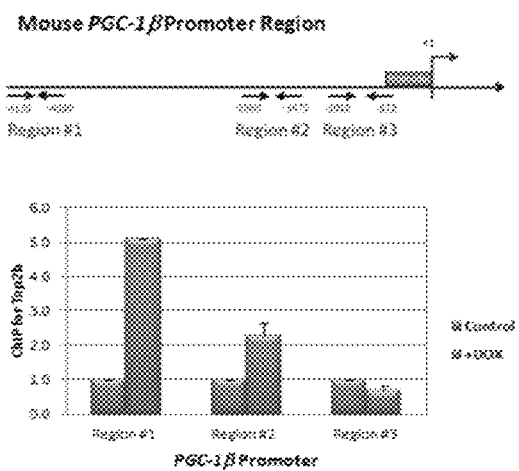
FIG. 7a-d e.

SEQUENCE LISTING

```
<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
atatggtaca gcaacaaagc atttgacata                                       30

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
tcattgggag gccagagcat c                                                21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tcatggatgt gctgggttag                                                  20

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
cagatggttg cttgcactag a                                                21

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
ccacggaaag aatcatgagg                                                  20

<210> SEQ ID NO 6
<211> LENGTH: 20
<212> TYPE: DNA
<213> ORGANISM: Artificial Sequence
```

<220> FEATURE:
<223> OTHER INFORMATION: Synthetic primer

<400> SEQUENCE: 6
aaccgccaca tttgtttagg                                           20

<210> SEQ ID NO 7
<211> LENGTH: 25
<212> TYPE: DNA
<213> ORGANISM: Artificial Sequence
<220> FEATURE:
<223> OTHER INFORMATION: Synthetic primer

<400> SEQUENCE: 7
ttcctctcta agcgttactt cactg                                     25

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
ctctttcaac tccaatccac tctg                                      24

<210> SEQ ID NO 9
<211> LENGTH: 30
<212> TYPE: DNA
<213> ORGANISM: Artificial Sequence
<220> FEATURE:
<223> OTHER INFORMATION: Synthetic primer

<400> SEQUENCE: 9
attcagtagc tggtgcatag caggtgctca                                30

<210> SEQ ID NO 10
<211> LENGTH: 30
<212> TYPE: DNA
<213> ORGANISM: Artificial Sequence
<220> FEATURE:
<223> OTHER INFORMATION: Synthetic primer

<400> SEQUENCE: 10
ggctctgtca cttagtagat ctgaagtgga                                30

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gtgccggaac aaaaggtagt                                           20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
ccagcacgct tttaaggaac                                           20

```
<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
aaccgtccag ccttttcagt                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tcagcctccc ttgtaccttg                                               20
```

TOPOISOMERASE 2B AS A PREDICTOR OF SUSCEPTIBILITY TO ANTHRACYCLINE-INDUCED CARDIOTOXICITY

This application claims the benefit of U.S. Provisional Patent Application No. 61/752,664, filed Jan. 15, 2013 the entirety of which is incorporated herein by reference.

BACKGROUND OF THE INVENTION

1. Field of the Invention

The present invention relates generally to the field of molecular biology, toxicology and oncology. More particularly, it concerns methods for predicting anthracycline cardiotoxicity in patients.

2. Description of Related Art

Anthracyclines, such as Doxorubicin, are still widely used in modern cancer treatments, despite the advent of targeted therapies (Yeh et al., 2009, Force et al., 2011). However, a dose-dependent cardiotoxicity often limits their clinical use. Doxorubicin's cellular target is Topoisomerase II (Top2) (Tewey et al., 1984). It binds both DNA and Top2 to form the ternary Top2-doxorubicin-DNA cleavage complex, which triggers cell death. There are two Top2 enzymes, Top2a and Top2b. Top2a, a known marker of cell proliferation, is overexpressed in tumors but not detectable in quiescent tissues (Capranico et al., 1992, Lyu et al., 2006). Thus, Top2a is thought to be the molecular basis of doxorubicin's anticancer activity.

Doxorubicin was postulated to induce cardiotoxicity through redox-cycling and generation of reactive oxygen species (ROS) (Singal et al., 1998). The ROS hypothesis, however, has been tempered by a series of studies in which ROS scavenger treatment failed to prevent cardiac toxicity caused by doxorubicin (Myers et al., 1983, Martin et al., 2009). Thus, the mechanism cardiotoxicity caused by anthracyclines, such as doxorubicin, has remained elusive and to date there is no method available to predict whether a patient will develop heart damage as a result of an anthracycline-based therapy.

SUMMARY OF THE INVENTION

Embodiments of the invention stem from the recognition that Top2b is the most physiologically relevant target of anthracycline compounds in heart tissue. Accordingly, assessment of Top2b expression level can be used to predict whether a subject is at risk for developing cardiotoxicity in response to anthracycline-based therapeutics. Furthermore, studies detailed here demonstrate that the cardioprotective compound dexrazoxane functions (at least in part) by reducing Top2b protein levels in heart tissue. Accordingly, a subject identified to be at high risk of anthracycline-induced cardiotoxicity (e.g., a subject having elevated Top2b expression) can be treated with an agent that reduces Top2b levels, such as dexrazoxane, to reduce the risk of anthracycline-induced cardiotoxicity.

Thus, in a first embodiment there is provided a method for treating a subject having a cancer comprising a) testing the subject's blood to determine the subject's Top2b expression level as compared to a reference; and b) administering an anthracycline therapeutic to the subject. For example, a level of Top2b in blood of the subject that is higher than the reference level, would indicate that the subject comprises a biomarker for cardiotoxicity.

In a further embodiment there is provided a method of determining whether a subject has a biomarker for anthracycline cardiotoxicity comprising (a) obtaining a blood sample from a subject; and (b) measuring Top2b in the sample, wherein a level of Top2b in the sample that is higher than a reference level indicates that the subject comprises a biomarker of anthracycline cardiotoxicity. In a further aspect, a method additionally comprises (c) identifying the subject as having a biomarker of anthracycline cardiotoxicity if the level of Top2b in the sample is higher than a reference level. For example, identifying a subject as having a biomarker can comprise providing a report (e.g., a written, oral or electronic report). In some cases, the report is provided to a doctor, a hospital, an insurance company or to the subject.

In still a further embodiment a method of treating a subject having a cancer is provided comprising: a) identifying a subject whose blood is determined to comprise an elevated Top2b expression level as compared to a reference; and b) administering a cardioprotective agent to the subject. For example, in some aspects, the cardioprotective agent is an agent that reduces Top2b protein levels in the subject (e.g., dexrazoxane). In some aspects, the method further comprises c) administering an anthracycline therapeutic to the subject. For example, the anthracycline therapeutic can be administered about 2, 4, 6, 8, or 10 hours after the cardioprotective agent (e.g., with-in 24 hours of the dexrazoxane treatment).

In a further embodiment a kit is provided comprising: (a) an anti-Top2b antibody or a nucleic acid molecule that specifically hybridizes to a Top2b RNA (e.g., a primer pair that can be used to amplify a Top2b sequence); and (b) a metered amount of an anthracycline therapeutic (e.g., doxorubicin) or an agent that reduces Top2b expression level (e.g., dexrazoxane). In some aspects, a kit further comprises operating instructions, such as instructions comprise a chart of reference levels of Top2b expression.

Aspects of the embodiments concern anthracycline therapeutics, such as those comprised in a pharmaceutically acceptable carrier. For example, in some aspects, the anthracycline therapeutic is comprised in a liposome. Examples of anthracycline therapeutics include, without limitation, daunorubicin, doxorubicin, epirubicin, idarubicin, valrubicin, and mitoxantrone.

Certain aspects of the embodiments concern administration of a cardioprotective agent to a subject (e.g., in conjunction with an anthracycline therapeutic). For example, the cardioprotective agent can be an agent that reduces Top2b protein levels in the subject. Agents that reduce Top2b protein levels include, without limitation, small molecules, such as dexrazoxane, and interfering nucleic acids that reduce Top2b expression (e.g., Top2b-targeted small interfering RNAs (siRNA), small hairpin RNAs (shRNA) or antisense nucleic acids).

In certain aspects, a subject being treated with an anthracycline therapeutic is further tested to detect any potential cardiac damage from the therapy. For example, the subject can be tested after each administration of anthracycline. In some aspects, the frequency of such testing is increased in a subject identified to have a biomarker of anthracycline-induced cardiotoxicity.

Certain aspects of the embodiments concern subjects that have been tested to determine a level of Top2b expression. In some aspects, Top2b expression is measured in a whole blood, a blood cell fraction, serum or a tissue sample (e.g., a muscle or cardiac biopsy) from the subject. In some aspects, a method of the embodiments can comprise obtaining a biological sample from a subject. It will be recognized that a sample may be directly obtained from a subject (e.g., by drawing blood from a subject) or may be obtained by a third party (e.g., a doctor or laboratory).

In certain aspects, testing to determine a level of Top2b expression comprises determining a level of Top2b protein expression. In other aspects, testing can comprise determining a level of Top2b mRNA expression. In still further aspects, a level of Top2b expression can be determined indirectly by detecting a genomic mutation that increased or decreased Top2b expression (e.g., a deletion, substitution, amplification or insertion). Methods for determining Top2b protein or mRNA expression or for detecting a genomic mutations that effects Top2b expression level are well known in the art and further detailed herein below.

Certain aspects of the embodiments concern subject that have a cancer. For example, in some aspects, the cancer can be a cancer that comprises an elevated level of Top2a expression relative to a reference. In some aspects, the cancer is a bladder cancer, breast cancer, lung cancer, stomach cancer, ovarian cancer, bladder cancer, Hodgkin's lymphoma, non-Hodgkin's lymphoma, cervical cancer, uterine cancer, prostate cancer, pancreatic cancer, adrenocortical cancer, liver cancer, Kaposi's sarcoma, Ewing's sarcoma, mesothelioma, multiple myeloma, a leukemia and other cancer that requires an anthracycline-containing treatment regimen.

In further aspects, a method of the embodiments further comprises administering an additional anticancer therapy to a subject. For example, the additional anticancer therapy can comprise radiation therapy, chemotherapy, immunotherapy or surgery.

In certain aspects, a subject of the embodiments is a canine, feline, equine, bovine or human subject. In some aspects, the subject is diagnosed with or was previously diagnosed with a cancer.

As used here a "biomarker" of anthracycline-induced cardiotoxicity references to an indicator that a subject has an increased risk of developing cardiotoxicity upon treatment with an anthracycline therapeutic. For example, in some aspects, a subject having a level of Top2b protein in the blood of over 0.4 ng/µg is identified as having a biomarker of anthracycline-induced cardiotoxicity and is at increased risk for developing cardiotoxicity in response to anthracycline-based therapy.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1a-f: Time-dependent changes in transcriptome following acute doxorubicin treatment. a. Ingenuity pathway analysis of changes in transcriptome in cardiomyocytes isolated from mice treated with 25 mg/kg doxorubicin for 16 h. b. Representative images of DSBs in sections of hearts from mice with different Top2b genotypes. The numbers of γ-H2AX-positive nuclei and the total nuclei were counted. Quantitative data were shown in the bar graph. Scale bar 50 µm. c. Apoptosis was detected by using the TUNEL assay on heart sections. The TUNEL-positive nuclei (red) and total nuclei per section were counted. Quantitative data were summarized in the bar graph. Scale bar 200 µm. d. Ingenuity pathway analysis of changes in transcriptome in cardiomyocytes isolated from mice treated with 25 mg/kg doxorubicin for 72 h. e. RT-qPCR validation of selected genes involved in mitochondria biogenesis and function. ΔΔCt method was used to analyze data. f. Western blot analysis of Ndufa3, Atp5a and Sdha in mitochondria isolated from cardiomyocytes. Coxi4 was used as a control. One way ANOVA was used to determine statistical significance. One asterisk indicated that the p-value was less than 0.05 and two asterisks indicated that the p-value was less than 0.001 (b, c, e).

FIGS. 2a-e: Changes in mitochondrial function and structure with acute doxorubicin treatment a. Doxorubicin-induced alteration in mitochondrial membrane potential changes. Representative images (200×) of JC-1 staining of cardiomyocytes isolated from mice treated with doxorubicin (25 mg/kg for 72 h) or PBS. b. Representative transmission electron micrographs of heart sections from mice treated doxorubicin (25 mg/kg for 72 h) or PBS. Scale bar 1 µm. Development of heart failure following chronic doxorubicin exposure Effect of chronic doxorubicin treatment (5 mg/kg, once a week for 5 weeks) on left ventricular end systolic volume (c), end diastolic volume (d), or ejection fraction (e). Bar represented mean±SEM and asterisks indicated significant difference (p<0.01).

FIG. 3: a. Top2b expression in the hearts by immunofluorescence. Representative images of Top2b expression in the hearts of a wildtype mouse (upper panels) and a mouse with Top2b deletion in the cardiomyocytes (lower panels). Hearts were embedded in OCT and snap-frozen in liquid nitrogen. Heart sections of 5 µm-thick were stained with an antibody against Top2b (BD Biosciences), followed by detection with a secondary antibody conjugated with Alexa Fluor 546 (red). The nuclei were stained with DAPI. Scale bars=50 µm. b. Top2b expression in the hearts by Western blot. Expression of Top2b in the heart of wildtype mice and mice with one copy or both copies of Top2b deleted in the cardiomyocytes.

FIGS. 4a-c: a. Phospho-p53 expression in the hearts Increased expression of phospho-p53 in the cardiomyocytes isolated from Top2b$^{+/+}$ and Top2b$^{\Delta/\Delta}$ mice 16 hr after treatment with doxorubicin (25 mg/kg) or drug vehicle. b. RT-qPCR validation of TRP53INP1 induction TRP53INP1 expression in cardiomyocytes isolated from the heart of mice 16 hrs after treatment with doxorubicin (25 mg/kg). Graph shows relative mRNA levels for Top2b$^{+/+}$ Control, Top2b$^{+/+}$ Dox, Top2b$^{\Delta/\Delta}$ Control, and Top2b$^{\Delta/\Delta}$ Dox (from left to right). ΔΔCt method was used to analyze the expression data. c. RT-qPCR validation of p53 pathway gene induction. Enhanced expression of other p53-activated-genes was determined with RT-qPCR. Extraction of total RNA from cardiomyocytes isolated from mouse heart was performed 16 hrs after doxorubicin treatment (25 mg/kg, ip). Graph shows relative mRNA levels for Top2b$^{+/+}$ Control, Top2b$^{+/+}$ Dox, Top2b$^{\Delta/\Delta}$ Control, and Top2b$^{\Delta/\Delta}$ Dox (from left to right).

FIGS. 5a-c: a. Determination of oxygen consumption rate (OCR). Cardiomyocytes were isolated from hearts of Top2b$^{+/+}$ and Top2b$^{\Delta/\Delta}$ mice 72 hrs after treatment with doxorubicin (25 mg/kg; right bars) or drug vehicle (left bars). The cardiomyocytes were seeded in 96-well plates for oxygen consumption measurement using a Seahorse XF96 instrument. OCR was measured continuously for 90 min in about 106 cardiomyocytes from each mouse. The basic OCR was hardly changed during the 90 min measurement, therefore, the OCR at 90 min was compared among the groups. After measurement, the number of cells was counted. Results were normalized as pmoles of oxygen consumed per min per 1,000 cells. Bars represent means±SEM. Asterisk indicates statistically significant difference (p<0.05). b. ROS production in the hearts. Representative images of heart sections stained with Dihydroethidium (DHE), which, after being oxidized, intercalates into DNA and stains the nuclei red. Hearts were harvested 16 hrs after doxorubicin treatment (25 mg/kg) and snap-frozen as described. Heart sections were stained with DHE immediately. Sections of hearts from un-treated controls were not stained with DHE. c. Quantification of ROS production in FIG. 5b. The numbers of DHE-positive and total nuclei were counted as described and the percentage of DHE-positive nuclei was determined. Quantitative data (mean±SEM) were shown as a bar graph below the images. The asterisks indicated statistically significant differences (*p<0.05) or (**p<0.001). Scale bar=50 µm.

FIGS. 6a-e: a. Schematic of chronic doxorubicin treatment protocol. All mice received a baseline MRI scan first. Tamoxifen was then administered by gavage at a dose of 25 mg/kg, once a day for 5 consecutive days. Two weeks after the last dose of Tamoxifen mice were given another MRI scan to confirm the cardiac function was not affected by Tamoxifen. Doxorubicin treatment (5 mg/kg, once a week for 5 weeks) was started one week after the second MRI scan. Two weeks after the last dose of doxorubicin, mice received a third MRI scan to assess cardiac function. After the last MRI scan, mice were sacrificed and the hearts were removed and examined for histological changes and Top2b expression. b. RT-qPCR of genes involved in mitochondrial biogenesis. Mice were treated with doxorubicin (5 mg/kg) once a week for 5 weeks. Cardiomyocytes were isolated from the heart 72 hr after the last dose. Total RNA was extracted for RTqPCR analysis of genes important for the function and structure of the mitochondria. For each mRNA shown relative expression is graphed for Top2b$^{+/+}$ Control, Top2b$^{+/+}$ Dox, Top2b$^{\Delta/\Delta}$ Control, and Top2b$^{\Delta/\Delta}$ Dox (from left to right). One way ANOVA was used to determine statistical significance (p<0.05). Error bars indicated STDEV. The asterisks indicated a significant difference (p<0.05). c. ROS production and quantitation. Representative images of heart sections stained with Dihydroethidium (DHE), which, after oxidation, intercalated into DNA and stained the nuclei red. Mice were treated with doxorubicin (5 mg/kg) once a week for 5 weeks. Cardiomyocytes were isolated from the heart 16 h after the last dose. Hearts were snap-frozen as described. Heart sections were stained with DHE immediately. The numbers of DHE-positive and total nuclei were counted as described and the percentage of DHE-positive nuclei was determined. The bar graph showed the quantitative data (mean±SEM). The asterisks indicated statistically significant differences (p<0.05). Scale bar=100 µm. d. EM study of the hearts. Representative transmission electron micrographs of Top2b$^{+/+}$ and Top2b$^{\Delta/\Delta}$ heart sections from mice treated doxorubicin (5 mg/kg, once a week for 5 weeks) or PBS. Hearts were harvested 72 hrs after the last dose and fixed for TEM examination. Scale bar=1 µm. e. Fibrosis in the hearts. Representative images of heart sections stained with Masson's Trichrome. Mice were treated with doxorubicin (5 mg/kg) once a week for 5 weeks. Hearts were harvested 72 h after the last dose and fixed in 4% paraformaldehyde for 24 h. Hearts were then embedded in paraffin and sectioned. Heart sections (5 µm) were then stained with Masson's Trichrome to examine collagen fibers. In the heart of Top2b+/+ mice doxorubicin treatment caused patchy fibrosis. A magnified area of fibrosis (insert) was pointed by the yellow arrow. Scale bar=500 µm.

FIGS. 7a-e: a, b. PGC-1 expression in HL-1 cells. Reduced expression of PGC-1α (a) or PGC-1β (b) in HL-1 cells after treatment with doxorubicin (1 µm; right bars) or control treatment (left bars) for 2 or 4 hours. Expression was measured with RT-qPCR. c, d. CHiP analysis in HL-1 cells. HL-1 cardiomyocytes were treated with (right bars) or without (left bars) DOX (1 mM) for 2 hrs and isolated for ChIP using the Top2β antibody. The eluted DNA and Input were PCR amplified to detect specific promoter regions represented in the schematic above the respective ChIP data. In the presence of DOX, the Top2b is readily bound to Region #1 and Region #3 of the PGC-1α promoter (c) and Region #1 and #2 of the PGC-1β promoter (d). e. CHiP study in cardiomyocytes. Cardiomyocytes were isolated from control (n=4) and Dox-treated (n=4) mice and subject to ChIP with the Top2b antibody. The data represent real-time PCR ratios for the fold-enrichment of Top2b at the respective promoters. Top2β binds the Region #1 of the PGC-1α and PGC-1β promoters efficiently following Dox treatment.

DESCRIPTION OF ILLUSTRATIVE EMBODIMENTS

I. The Present Invention

Figure 4C:
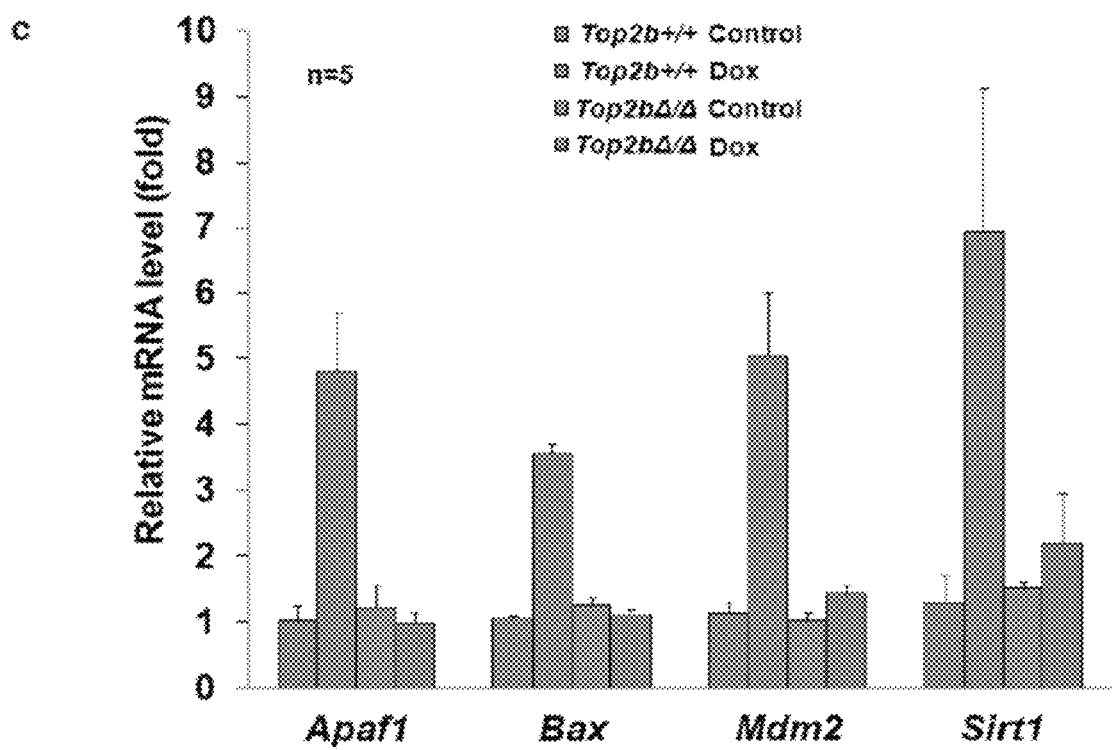

Anthracyclines, such as doxorubicin, are can be used as highly effective anticancer therapies. However, these compounds are known to cause damage to cardiomyocytes in a dose-dependent manner. Because of this patient's receiving anthracycline therapy, such as treatment with doxorubicin, have to be carefully monitored to detect signs of heart damage and/or administered secondary agents to help limit cardiac damage. This dangerous side effect of anthracycline-therapy has been the major limitation of its clinical usage and no method was previously known for predicting whether a patient would display cardiotoxicity in response to therapy or how serious cardiotoxicity would be.

Studies detailed herein demonstrate that cardiomyocyte-specific deletion of Top2b expression was able to protect cardiomyocytes from doxorubicin-induced DNA double strand breaks. Cardiomyocytes that lacked Top2b expression also showed changes in their transcriptome that are responsible for defective mitochondrial biogenesis and ROS formation. Furthermore, deletion of Top2b protected mice from development of doxorubicin-induced progressive heart failure, suggesting that Top2b is the molecular basis of doxorubicin-induced cardiotoxicity. In view of the results studies were undertaken to determine if Top2b expression would be a useful biomarker for predicting cardiotoxicity. Since detection of Top2b in patient's heart would be difficult and invasive, ELISA was used to determine the peripheral blood expression level of Top2b as a surrogate for Top2b expression in the heart. Studies shown in FIG. 8 demonstrate that patients with low Top2b level in the peripheral blood are more resistant to doxorubicin-induced cardiotoxicity, whereas patients with high Top2b level are much more sensitive to doxorubicin. Thus, Top2b expression level (such the level of Top2b protein measured in the peripheral blood) can be used as a genetic marker to predict susceptibility to doxorubicin-induced cardiotoxicity.

The new methods provided here could vastly improve therapeutic use of anthracyclines compounds such as doxorubicin. Before treatment, patients can be tested to determine their Top2b expression level. If Top2b level is low, then patients can safely receive a high dose of therapeutic, such as up to 450 $mg/m^2$ of doxorubicin even without regular monitoring for cardiac damage. On the other hand, if Top2b expression level is high, then patients should receive a lower initial dose of drug, intensive monitoring for cardiac damage and cardiac protective medication as they receive increased amounts of anthracycline-therapy.

II. Detecting Gene Expression

In certain embodiments, methods provided herein concern detecting determining a gene expression in a subject, in particular method concern detecting and/or quantifying Top2b expression. For example, in some embodiments, determining a Top2b level in a sample comprises quantifying Top2b RNA or protein expression. In some aspects, quantifying Top2b expression comprises determining Top2b expression relative to a reference RNA or protein. Elevated Top2b expression in a subject indicates that the subject is at increased risk of anthracycline-induced cardio toxicity. Accordingly, such a subject should receive a lower dosage of an anthracycline therapeutic and/or should receive additional cardioprotective agents or increased monitoring for cardiac damage. Alternatively, subjects with elevated Top2b levels could be selected to treatment with a non-anthracycline therapeutic. On the other hand, a subject with low expression levels of Top2b can be safely administered higher levels of anthracycline therapeutics and can therefore be selected for anthracycline therapies and, in particular, for high dose anthracycline therapies.

It is known to those of skill in the art that any clinical diagnosis is not necessarily be made on the basis of a single method in isolation. Accordingly, methods of the embodiments can comprise determining or obtaining the expression level or presence of two, three or more biomarkers and/or on one or more clinical symptoms in additional a Top2b expression level to assess risk for cardiovascular damage in a subject.

A. Nucleic Acid Detection

In some embodiments, assessing expression of Top2b, can involve quantifying mRNA expression. For example, reverse transcription (RT) of RNA to cDNA followed by relative quantitative PCR™ (RT-PCR™) can be used to determine the relative concentrations of specific mRNA (e.g., a Top2b coding RNA). By determining that the concentration of a specific mRNA varies relative to a reference RNA (e.g., an RNA encoding control gene such as GAPDH), it is shown that the gene encoding the specific mRNA species is differentially expressed. In certain aspects, mRNA expression can be quantified relative to the expression of such a reference mRNA.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

Northern blotting techniques for detecting RNA expression are also well known to those of skill in the art. Northern blotting involves the use of RNA as a target. Briefly, a probe is used to target an RNA species that has been immobilized on a suitable matrix, often a filter of nitrocellulose. The different species should be spatially separated to facilitate analysis. This often is accomplished by gel electrophoresis of nucleic acid species followed by "blotting" on to the filter. Subsequently, the blotted target is incubated with a probe (such as a labeled probe) under conditions that promote denaturation and rehybridization. Because the probe is designed to base pair with the target, the probe will binding a portion of the target sequence under renaturing conditions. Unbound probe is then removed, and detection is accomplished.

In some embodiments, nucleic acids are quantified following gel separation and staining with ethidium bromide and visualization under UV light. In some embodiments, if the nucleic acid results from a synthesis or amplification using integral radio- or fluorometrically-labeled nucleotides, the products can then be exposed to x-ray film or visualized under the appropriate stimulating spectra, following separation.

In some embodiments, visualization is achieved indirectly. Following separation of nucleic acids, a labeled nucleic acid is brought into contact with the target sequence. The probe is conjugated to a chromophore or a radiolabel. In another embodiment, the probe is conjugated to a binding partner, such as an antibody or biotin, and the other member of the binding pair carries a detectable moiety. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present embodiments.

B. Detection of Protein

In some aspects, methods of the embodiments concern detection of the expression of Top2b protein. For example, immunodetection methods for binding, purifying, removing, quantifying and/or otherwise generally detecting protein components such as Top2b can be employed. Antibodies prepared in accordance with the present embodiments may be employed to detect Top2b. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

In general, the immunobinding methods include obtaining a sample suspected of containing a Top2b protein, polypeptide and/or peptide, and contacting the sample with a first anti-Top2b antibody in accordance with the present embodiments, under conditions effective to allow the formation of immunocomplexes. The antibody will preferably be linked to a solid support, such as in the form of a column matrix, and the sample suspected of containing biomarker protein antigenic component will be applied to the immobilized antibody. The unwanted components will be washed from the column, leaving the antigen immunocomplexed to the immobilized antibody, biomarker protein antigen is then collected by removing the protein and/or peptide from the column.

The immunobinding methods also include methods for detecting and quantifying the amount of a Top2b in a sample. Here, one would obtain a sample and contact the sample with an antibody and then detect and quantify the amount of immune complexes formed under the specific conditions.

In terms of antigen detection, the biological sample analyzed may be any sample that is suspected of containing a cell expressing CD133, such as a serum or whole blood sample, a tissue extract or another biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any Top2b protein antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277, 437; 4,275,149 and 4,366,241, each incorporated herein by reference. Of course, one may find additional advantages through the use of a secondary binding ligand such as a second antibody and/or a biotin/avidin ligand binding arrangement, as is known in the art.

In some embodiments, a Top2b antibody (e.g., an anti-Top2b antibody) employed in the detection may itself be linked to a detectable label, wherein one would then simply detect this label, thereby allowing the amount of the primary immune complexes in the composition to be determined. In some embodiments, the first antibody that becomes bound within the primary immune complexes may be detected by means of a second binding ligand that has binding affinity for the antibody. In certain embodiments, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR methodology. The PCR™ method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR™ reaction with suitable primers with appropriate controls. At least in theory, the enormous amplification capability and specificity of PCR™ can be utilized to detect a single antigen molecule.

The immunodetection methods of the present embodiments have evident utility in the diagnosis and prognosis of conditions such as various forms of inflammatory disease, such as KD. Here, a biological and/or clinical sample suspected of containing a Top2b biomarker protein, polypeptide, peptide and/or mutant is used. However, these embodiments also have applications to non-clinical samples, such as in the titering of antigen or antibody samples, for example in the identification of cellular mediators of inflammation.

III. Therapeutic Administration

As detailed supra certain aspects of the embodiments involve the use of anthracycline-based therapies. For example, in some aspects, a subject is selected for administration of an anthracycline-based anti-cancer therapy. Anthracyclines for use accorind to the embodiments include, without limitation, daunorubicin, doxorubicin, epirubicin, idarubicin, valrubicin, or mitoxantrone.

In some embodiments, an effective amount of an anthracyclines agent or a combination of anthracyclines is administered to a subject. The term "effective amount" as used herein is defined as the amount of anthracycline that is necessary to result in a physiological change in the patient to which it is administered. The term "therapeutically effective amount" as used herein is defined as the amount of an anthracycline that eliminates, decreases, delays, or minimizes adverse effects of a disease (e.g., cancer). A skilled artisan readily recognizes that in many cases methods of the invention may not provide a cure but may only provide partial benefit, such as alleviation or improvement of at least one symptom. In some embodiments, a physiological change having some benefit is also considered therapeutically beneficial. It will additionally be clear that a therapeutically effective amount may be dependent upon the inclusion of additional therapeutic regimens administered concurrently or sequentially. Thus, it will be understood that in certain embodiments a physical change may constitute an enhanced effectiveness of a second therapeutic treatment.

For example, anthracyclines may be administered to a subject per se or in the form of a pharmaceutical composition. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen. In particular, in some aspects, anthracyclines are formulated in liposomal compositions.

In some aspects methods of the invention concern systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

A. Effective Dosages

Anthracyclines therapies of the embodiments will generally be used in an amount effective to achieve the intended purpose (therapeutic anti-cancer efficacy). For use to treat or prevent a disease condition, the molecules of the embodiments, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data. In some aspects of the embodiments dosing of anthracyclines therapeutics may be guided by measuring the level of Top2b in a sample from a subject. For example, in a subject comprising a high level Top2b protein expression of could be administered a low initial dose of anthracyclines, such as Dox. Anthracycline dosing will vary depending upon the type of cancer to be treated and guidelines for the treatment of a wide range of cancers are will known in the art.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

B. Pharmaceutical Preparations

Pharmaceutical compositions of the present invention may comprise an effective amount of an anthracycline dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical compositions will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compositions of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In particular embodiments, prolonged absorption of an injectable composition can be brought about by the use in the compositions of agents delaying absorption, such as, for example, aluminum monostearate, gelatin or combinations thereof.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The Role of Top2b in Doxorubicin Cardiotoxicity

To investigate the role of Top2b in doxorubicin-induced cardiac toxicity, a mouse model was established with cardiomyocyte-specific deletion of Top2b (MHCMerCreMer Top2b$^{flox/flox}$ by crossing Top2b$^{flox/flox}$ mice (10) with MHC-MerCreMer mice (11). MerCreMer Top2b$^{flox/flox}$ mice were viable, fertile, normal in size, and do not display any gross physical or behavioral abnormalities. Cardiomyocyte-specific Cre induction was carried out by treating mice with tamoxifen (25 mg/kg gavage, once a day for 5 consecutive days). Two weeks after the last dose of tamoxifen, hearts were harvested for detection of Top2β.

Hearts were embedded in OCT and snap frozen in liquid nitrogen. Frozen sections were stained with an anti-Top2b antibody to confirm deletion of Top2b from the cardiomyocytes. Top2b protein was readily detected in the nuclei of heart section of a representative Top2b$^{+/+}$ mouse (FIG. 3a). However, the heart section of the Top2b$^{\Delta/\Delta}$ mouse had a marked reduction in the number of Top2b-positive nuclei. The reduction was also evident in whole heart cell lysate detected using western blot (FIG. 3b). Because Cre expression is driven by a cardiomyocyte-specific promoter, endothelial cells and other stromal cells still expressed Top2b in the Top2b$^{\Delta/\Delta}$ mouse. Top2b is apparently not required for normal homeostasis of adult hearts as the Top2b$^{\Delta/\Delta}$ mouse survived for more than ten months in excellent health with preserved ejection fractions.

Microarray-based Ingenuity pathway analysis was next used to study the effect of doxorubicin treatment in the Top2b$^{+/+}$ and Top2b$^{\Delta/\Delta}$ heart in an unbiased way. Mice were treated with tamoxifen for 5 consecutive days. Two weeks after the last dose of tamoxifen, mice were treated with doxorubicin (25 mg/kg, i.p.) and sacrificed 16 hrs later. Cardiomyocytes were prepared from excised heart and mRNAs were extracted for microarray analysis. Ingenuity pathway analysis of microarray data based on expression changes (>1.5 fold) of 59,306 genes upon doxorubicin treatment identified perturbation (mainly activation) in p53 and β-adrenergic signaling pathways in Top2b$^{+/+}$ cardiomyocytes (left bars), but not in Top2bΔ/Δ cardiomyocytes (center bars) (FIG. 1a, FIG. 4a, and Table 1). No difference was found between untreated Top2b$^{+/+}$ and Top2b$^{\Delta/\Delta}$ cardiomyocytes (right bars). Of particular interest is a 200 fold up-regulation of the transcript encoding p53DINP1, a p53-inducible gene that regulates apoptosis (Sohal et al., 2001) (FIG. 4b). There were also increases in the transcript of Apaf1, Bax, and Fas, genes important in the apoptosis pathway (Ogasawara et al., 1983) (FIG. 4c). Both p53DINP1, Apaf1, Bax, Mdm2, and Fas up-regulation were only observed in doxorubicin-treated Top2b$^{+/+}$, but not Top2b$^{\Delta/\Delta}$ cardiomyocytes. This is consistent with the previous observation that doxorubicin and Top2b formed a DNA ternary cleavage complex to induce DNA double strand breaks (DSBs), leading to cell death (9).

TABLE 1

Up-regulated genes (>1.5 fold) associated with p53 signaling pathway 16 hrs after doxorubicin treatment in Top2b$^{+/+}$ cardiomyocytes.

| Symbol | Entrez Gene Name |
| --- | --- |
| AKT3 | v-akt murine thymoma viral oncogene homolog 3 (protein kinase B, gamma) |
| APAF1 | apoptotic peptidase activating factor 1 |
| ATR | ataxia telangiectasia and Rad3 related |
| BAX | BCL2-associated X protein |
| BCL2L1 | BCL2-like 1 |
| BIRC5 | baculoviral IAP repeat containing 5 |
| CCND1 | cyclin D1 |
| CDKN1A | cyclin-dependent kinase inhibitor 1A (p21, Cip1) |
| CSNK1D | casein kinase 1, delta |
| FAS | Fas (TNF receptor superfamily, member 6) |
| GADD45A | growth arrest and DNA-damage-inducible, alpha |
| GADD45B | growth arrest and DNA-damage-inducible, beta |
| GADD45G | growth arrest and DNA-damage-inducible, gamma |
| GNL3 | guanine nucleotide binding protein-like 3 (nucleolar) |
| HIPK2 | homeodomain interacting protein kinase 2 |
| JMY | junction mediating and regulatory protein, p53 cofactor |
| MDM2 | Mdm2 p53 binding protein homolog (mouse) |
| PCNA | proliferating cell nuclear antigen |
| PIDD | p53-induced death domain protein |
| PIK3R1 | phosphoinositide-3-kinase, regulatory subunit 1 (alpha) |
| PIK3R5 | phosphoinositide-3-kinase, regulatory subunit 5 |
| PLAGL1 | pleiomorphic adenoma gene-like 1 |
| PTEN | phosphatase and tensin homolog |
| SIRT1 | sirtuin 1 |
| TNFRSF10A | tumor necrosis factor receptor superfamily, member 10a |
| TP53INP1 | tumor protein p53 inducible nuclear protein 1 |

Note:
TP53INP1 is also called p53DINP1. The list was generated by Ingenuity software, and none of the genes identified in the p53 pathway had an expression change that reached 1.5 fold in Top2b$^{\Delta/\Delta}$ cardiomyocytes.

The activation of DNA damage response pathway was confirmed by staining heart sections with antibody against γ-H2AX to detect DSBs (14). As shown, doxorubicin caused DSBs in the nuclei of Top2b$^{+/+}$ mice, but this was reduced by 60% in Top2b$^{\Delta/\Delta}$ mice (FIG. 1b). Furthermore, cell death after acute doxorubicin treatment was examined in Top2b$^{+/+}$ and Top2b$^{\Delta/\Delta}$ mice using an apoptosis detection kit (FIG. 1c). TUNELpositive nuclei were also reduced by 70% in the hearts of Top2b$^{\Delta/\Delta}$ mice compared with Top2b$^{+/+}$ mice. Thus, Top2b expression correlated with changes in transcriptome, DSBs, and apoptosis in cardiomyocytes.

To gain further insight into the pathogenesis of doxorubicin-induced cardiotoxicity, the transcriptome analysis was repeated 72 h following doxorubicin exposure. The Ingenuity pathway analysis of microarray data based on expression changes (>1.5 fold) of 59,306 genes upon doxorubicin treatment identified perturbation (mainly repression) in the mitochondria dysfunction and oxidative phosphorylation pathways in Top2b$^{+/+}$ cardiomyocytes (left bars), but not in Top2b$^{\Delta/\Delta}$ cardiomyocytes (middle bars). No difference was found between untreated Top2b$^{+/+}$ and Top2b$^{\Delta/\Delta}$ cardiomyocytes (right bars). There was a complete change in the ingenuity pathway profiles 72 h following doxorubicin exposure (FIGS. 1a,d). Early activation in the p53 pathway was replaced by mitochondrial dysfunction and oxidative phosphorylation pathways in the Top2b$^{+/+}$, but not Top2b$^{\Delta/\Delta}$ cardiomyocytes (FIGS. 1a,d and Table 2). Both peroxisome proliferative activated receptor, gamma, coactivator 1 α and β (PGC-1α and PGC-1β) were downregulated by 1.5 fold in the wild type, but not Top2b deleted, hearts after doxorubicin treatment. This was confirmed by qPCR of analysis of PGC-1α and PGC-1β transcripts (FIG. 1e). Erra, a downstream target of PGC-1, is also down-regulated in the doxorubicin-treated wild type, but not Top2b-deleted, cardiomyocytes. Consistent with the critical role exerted by PGC-1α and PGC-1β in mitochondrial biogenesis (Arany, Z. et al., 2006; Lai, L. et al., 2008), transcripts of key electron transport chains, such as Ndufa3 (NADH dehydrogenase 1 alpha subcomplex, 3, Complex1), Sdha (succinate dehydrogenase complex, subunit A, Complex II), and Atp5a (alpha subunit of Complex V) were decreased in the doxorubicin treated Top2b$^{+/+}$, but much less so in Top2b$^{\Delta/\Delta}$ cardiomyocytes (FIG. 1e). The changes in transcripts were also supported by reduction in the protein levels (FIG. 1f). Thus, in the presence of Top2b, doxorubicin caused decreases in transcripts of genes involved in the regulation of mitochondria biogenesis and function.

TABLE 2

Change in gene expression associated with mitochondrial dysfunction and oxidative phosphorylation pathways 72 hrs after doxorubicin treatment in Top2b$^{+/+}$ cardiomyocytes.

| Symbol | Entrez Gene Name |
|---|---|
| \multicolumn{2}{c}{Down-regulated Genes (>1.5 fold)} | |
| AIFM1 | apoptosis-inducing factor, mitochondrion-associated, 1 |
| APH1B | anterior pharynx defective 1 homolog B (*C. elegans*) |
| ATP5A1 | ATP synthase, H+ transporting, mitochondrial F1 complex, alpha subunit 1, cardiac muscle |
| ATP5B | ATP synthase, H+ transporting, mitochondrial F1 complex, beta polypeptide |
| ATP5C1 | ATP synthase, H+ transporting, mitochondrial F1 complex, gamma polypeptide 1 |
| ATP5J | ATP synthase, H+ transporting, mitochondrial Fo complex, subunit F6 |
| BACE1 | beta-site APP-cleaving enzyme 1 |
| CASP3 | caspase 3, apoptosis-related cysteine peptidase |
| COX17 | COX17 cytochrome c oxidase assembly homolog (*S. cerevisiae*) |
| COX5A | cytochrome c oxidase subunit Va |
| COX6A1 | cytochrome c oxidase subunit VIa polypeptide 1 |
| COX6A2 | cytochrome c oxidase subunit VIa polypeptide 2 |
| COX6B1 | cytochrome c oxidase subunit VIb polypeptide 1 (ubiquitous) |
| COX6C | cytochrome c oxidase subunit VIc |
| COX7A1 | cytochrome c oxidase subunit VIIa polypeptide 1 (muscle) |
| COX7A2 | cytochrome c oxidase subunit VIIa polypeptide 2 (liver) |
| COX7A2L | cytochrome c oxidase subunit VIIa polypeptides 2 like |
| COX7B | cytochrome c oxidase subunit VIIb |
| Cox8b | cytochrome c oxidase, subunit VIIIb |
| CPT1B | carnitine palmitoyltransferase 1B (muscle) |
| CYC1 | cytochrome c-1 |
| FURIN | furin (paired basic amino acid cleaving enzyme) |
| GPD2 | glycerol-3-phosphate dehydrogenase 2 (mitochondrial) |
| GPX4 | glutathione peroxidase 4 (phospholipid hydroperoxidase) |
| GSR | glutathione reductase |
| HSD17B10 | hydroxysteroid (17-beta) dehydrogenase 10 |
| HTRA2 | HtrA serine peptidase 2 |
| MAP2K4 | mitogen-activated protein kinase kinase 4 |
| MAPK8 | mitogen-activated protein kinase 8 |
| MAPK9 | mitogen-activated protein kinase 9 |
| MAPK10 | mitogen-activated protein kinase 10 |
| MT-CO2 | cytochrome c oxidase subunit II |
| MT-CO1 | cytochrome c oxidase subunit I |
| MT-CYB | cytochrome b |
| MT-ND4 | NADH dehydrogenase, subunit 4 (complex I) |
| MT-ND4L | NADH dehydrogenase, subunit 4L (complex I) |
| NCSTN | Nicastrin |
| NDUFA2 | NADH dehydrogenase (ubiquinone) 1 alpha subcomplex, 2, 8 kDa |
| NDUFA3 | NADH dehydrogenase (ubiquinone) 1 alpha subcomplex, 3, 9 kDa |
| NDUFA5 | NADH dehydrogenase (ubiquinone) 1 alpha subcomplex, 5, 13 kDa |
| NDUFA6 | NADH dehydrogenase (ubiquinone) 1 alpha subcomplex, 6, 14 kDa |
| NDUFA7 | NADH dehydrogenase (ubiquinone) 1 alpha subcomplex, 7, 14.5 kDa |
| NDUFA8 | NADH dehydrogenase (ubiquinone) 1 alpha subcomplex, 8, 19 kDa |
| NDUFA9 | NADH dehydrogenase (ubiquinone) 1 alpha subcomplex, 9, 39 kDa |
| NDUFA10 | NADH dehydrogenase (ubiquinone) 1 alpha subcomplex, 10, 42 kDa |
| NDUFA12 | NADH dehydrogenase (ubiquinone) 1 alpha subcomplex, 12 |
| NDUFA13 | NADH dehydrogenase (ubiquinone) 1 alpha subcomplex, 13 |
| NDUFAF1 | NADH dehydrogenase (ubiquinone) 1 alpha subcomplex, assembly factor 1 |
| NDUFB3 | NADH dehydrogenase (ubiquinone) 1 beta subcomplex, 3, 12 kDa |
| NDUFB4 | NADH dehydrogenase (ubiquinone) 1 beta subcomplex, 4, 15 kDa |
| NDUFB5 | NADH dehydrogenase (ubiquinone) 1 beta subcomplex, 5, 16 kDa |

TABLE 2-continued

Change in gene expression associated with mitochondrial dysfunction and oxidative phosphorylation pathways 72 hrs after doxorubicin treatment in Top2b$^{+/+}$ cardiomyocytes.

| Symbol | Entrez Gene Name |
|---|---|
| NDUFB6 | NADH dehydrogenase (ubiquinone) 1 beta subcomplex, 6, 17 kDa |
| NDUFB7 | NADH dehydrogenase (ubiquinone) 1 beta subcomplex, 7, 18 kDa |
| NDUFB9 | NADH dehydrogenase (ubiquinone) 1 beta subcomplex, 9, 22 kDa |
| NDUFB10 | NADH dehydrogenase (ubiquinone) 1 beta subcomplex, 10, 22 kDa |
| NDUFS1 | NADH dehydrogenase (ubiquinone) Fe—S protein 1, 75 kDa (NADH-coenzyme Q reductase) |
| NDUFS2 | NADH dehydrogenase (ubiquinone) Fe—S protein 2, 49 kDa (NADH-coenzyme Q reductase) |
| NDUFS3 | NADH dehydrogenase (ubiquinone) Fe—S protein 3, 30 kDa (NADH-coenzyme Q reductase) |
| NDUFS4 | NADH dehydrogenase (ubiquinone) Fe—S protein 4, 18 kDa (NADH-coenzyme Q reductase) |
| NDUFS5 | NADH dehydrogenase (ubiquinone) Fe—S protein 5, 15 kDa (NADH-coenzyme Q reductase) |
| NDUFS6 | NADH dehydrogenase (ubiquinone) Fe—S protein 6, 13 kDa (NADH-coenzyme Q reductase) |
| NDUFS7 | NADH dehydrogenase (ubiquinone) Fe—S protein 7, 20 kDa (NADH-coenzyme Q reductase) |
| NDUFS8 | NADH dehydrogenase (ubiquinone) Fe—S protein 8, 23 kDa (NADH-coenzyme Q reductase) |
| NDUFV1 | NADH dehydrogenase (ubiquinone) flavoprotein 1, 51 kDa |
| NDUFV2 | NADH dehydrogenase (ubiquinone) flavoprotein 2, 24 kDa |
| OGDH | oxoglutarate (alpha-ketoglutarate) dehydrogenase (lipoamide) |
| PARK2 | parkinson protein 2, E3 ubiquitin protein ligase (parkin) |
| PDHA1 | pyruvate dehydrogenase (lipoamide) alpha 1 |
| PRDX3 | peroxiredoxin 3 |
| PRDX5 | peroxiredoxin 5 |
| RHOT2 | ras homolog gene family, member T2 |
| SDHB | succinate dehydrogenase complex, subunit B, iron sulfur (Ip) |
| SDHD | succinate dehydrogenase complex, subunit D, integral membrane protein |
| SOD2 | superoxide dismutase 2, mitochondrial |
| TRAK1 | trafficking protein, kinesin binding 1 |
| TXN2 | thioredoxin 2 |
| UQCRC1 | ubiquinol-cytochrome c reductase core protein I |
| UQCRC2 | ubiquinol-cytochrome c reductase core protein II |
| UQCRFS1 | ubiquinol-cytochrome c reductase, Rieske iron-sulfur polypeptide 1 |
| ATP5D | ATP synthase, H+ transporting, mitochondrial F1 complex, delta subunit |
| ATP5E | ATP synthase, H+ transporting, mitochondrial F1 complex, epsilon subunit |
| ATP5F1 | ATP synthase, H+ transporting, mitochondrial Fo complex, subunit B1 |
| ATP5G1 | ATP synthase, H+ transporting, mitochondrial Fo complex, subunit C1 (subunit 9) |
| ATP5G2 | ATP synthase, H+ transporting, mitochondrial Fo complex, subunit C2 (subunit 9) |
| ATP5G3 | ATP synthase, H+ transporting, mitochondrial Fo complex, subunit C3 (subunit 9) |
| Atp5h (includes EG: 306478) | ATP synthase, H+ transporting, mitochondrial F0 complex, subunit d |
| ATP5I | ATP synthase, H+ transporting, mitochondrial Fo complex, subunit E |
| ATP5J2 | ATP synthase, H+ transporting, mitochondrial Fo complex, subunit F2 |
| ATP5L | ATP synthase, H+ transporting, mitochondrial Fo complex, subunit G |
| ATP6V0A1 | ATPase, H+ transporting, lysosomal V0 subunit a1 |
| ATP6V0A2 | ATPase, H+ transporting, lysosomal V0 subunit a2 |
| ATP6V0E1 | ATPase, H+ transporting, lysosomal 9 kDa, V0 subunit e1 |
| ATP6V1A | ATPase, H+ transporting, lysosomal 70 kDa, V1 subunit A |
| ATP6V1D | ATPase, H+ transporting, lysosomal 34 kDa, V1 subunit D |
| ATP6V1E2 | ATPase, H+ transporting, lysosomal 31 kDa, V1 subunit E2 |
| ATP6V1G1 | ATPase, H+ transporting, lysosomal 13 kDa, V1 subunit G1 |
| COX8A | cytochrome c oxidase subunit VIIIA (ubiquitous) |
| MT-ND2 | MTND2 |
| NDUFA1 | NADH dehydrogenase (ubiquinone) 1 alpha subcomplex, 1, 7.5 kDa |
| NDUFC2 | NADH dehydrogenase (ubiquinone) 1, subcomplex unknown, 2, 14.5 kDa |
| PPA1 | pyrophosphatase (inorganic) 1 |
| PPA2 | pyrophosphatase (inorganic) 2 |
| UQCR11 | ubiquinol-cytochrome c reductase, complex III subunit XI |
| UQCRHL | ubiquinol-cytochrome c reductase hinge protein-like |
| UQCRQ | ubiquinol-cytochrome c reductase, complex III subunit VII, 9.5 kDa |
| Ppargc1α | *Mus musculus* peroxisome proliferative activated receptor, gamma, coactivator 1 alpha |
| Ppargc1β | *Mus musculus* peroxisome proliferative activated receptor, gamma, coactivator 1 beta |

TABLE 2-continued

Change in gene expression associated with mitochondrial dysfunction and oxidative phosphorylation pathways 72 hrs after doxorubicin treatment in Top2b$^{+/+}$ cardiomyocytes.

| Symbol | Entrez Gene Name |
|---|---|
| \multicolumn{2}{c}{Up-regulatedGenes (>1.5 fold)} | |
| APP | amyloid beta (A4) precursor protein |
| CAT | Catalase |
| COX4I2 | cytochrome c oxidase subunit IV isoform 2 (lung) |
| COX8C | cytochrome c oxidase subunit VIIIC |
| CPT1A | carnitine palmitoyltransferase 1A (liver) |
| CYB5R3 | cytochrome b5 reductase 3 |
| GLRX2 | glutaredoxin 2 |
| MAOA | monoamine oxidase A |
| MAOB | monoamine oxidase B |
| PSEN1 | presenilin 1 |
| SNCA | synuclein, alpha (non A4 component of amyloid precursor) |
| UCP2 | uncoupling protein 2 (mitochondrial, proton carrier) |
| XDH | xanthine dehydrogenase |
| TCIRG1 | T-cell, immune regulator 1, ATPase, H+ transporting, lysosomal V0 subunit A3 |

Note:
The list was generated by Ingenuity software, and none of the genes identified in the 2 pathways had an expression change that reached 1.5 fold in Top2b$^{\Delta/\Delta}$ cardiomyocytes.

Figure 5C:
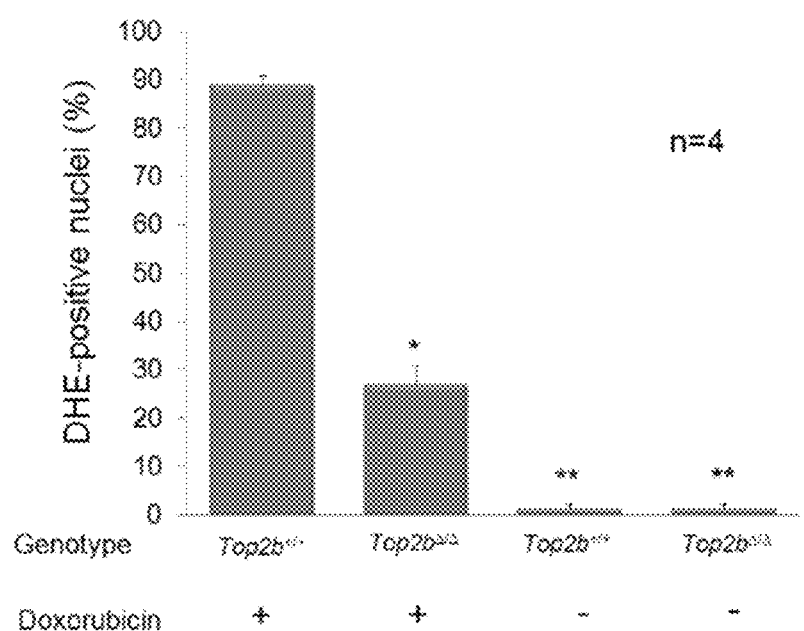

The reduction in transcripts that regulate mitochondria biogenesis and function was also confirmed by assay of mitochondrial membrane potential in isolated cardiomyocytes. JC-1, a lipophilic fluorochrome, was used to evaluate the status of the mitochondria membrane potential. JC-1 in monomeric form has emission maximum of 529 nm (green), whereas JC-1 at higher concentrations form aggregates with an emission maximum at 590 nm (red). The ratio of this green/red fluorescence is dependent on mitochondrial membrane potential, but independent of the shape, density, and size of mitochondria. These studies showed that the red fluorescence was markedly reduced in doxorubicin-treated cardiomyocytes from Top2b$^{+/+}$, but not Top2b$^{\Delta/\Delta}$ mice (FIG. 2a). The FACS-based red/green ratio was 0.82+/−0.12 in doxorubicin-treated wild type mitochondria as compared to 2.79+/−0.43 in control (n=3). The red/green ratio in the Top2b-deleted mitochondria was 2.09+/−0.06 vs 2.72+/−0.18 (doxorubicin vs. control, n=3). These results demonstrated that mitochondria failed to maintain their membrane potential in doxorubicin-treated wild type, but not Top2b deleted cardiomyocytes. The functional abnormality in mitochondria is also supported by electron microscopic examination of the hearts. FIG. 2b showed that marked mitochondria damage and vacuolization were present in doxorubicin-treated Top2b$^{+/+}$ mouse heart. However, there were minimal ultra-structural changes in similarly treated Top2b$^{\Delta/\Delta}$ heart. The ultrastructural changes were also supported by direct measurement of the oxygen consumption rate (OCR). As shown, OCR was significantly reduced in doxorubicin treated wild type, but not Top2b deleted cardiomyocytes (FIG. 5a). Thus, it is clear that Top2b is required for doxorubicin-induced ultra-structural and functional changes in the mitochondria.

The functional and structural changes in mitochondria following doxorubicin exposure suggested that ROS generation was a result of changes in transcriptome, not from redox cycling of doxorubicin as previously suggested. Generation of ROS in the hearts of doxorubicin-treated Top2b$^{+/+}$ and Top2b$^{\Delta/\Delta}$ mice was next investigated. The hearts were isolated on ice, embedded in OCT, snap frozen in liquid nitrogen, sectioned into 5 μm-thick slices, and ROS generation was detected immediately by using dihydroethidium (DHE). Doxorubicin treatment generated ROS in the hearts of Top2b$^{+/+}$ mice, but this was reduced by 70% in Top2b$^{\Delta/\Delta}$ mice (FIGS. 5b,c). These results clearly established that ROS generation was also dependent on Top2b.

Figure 6E:
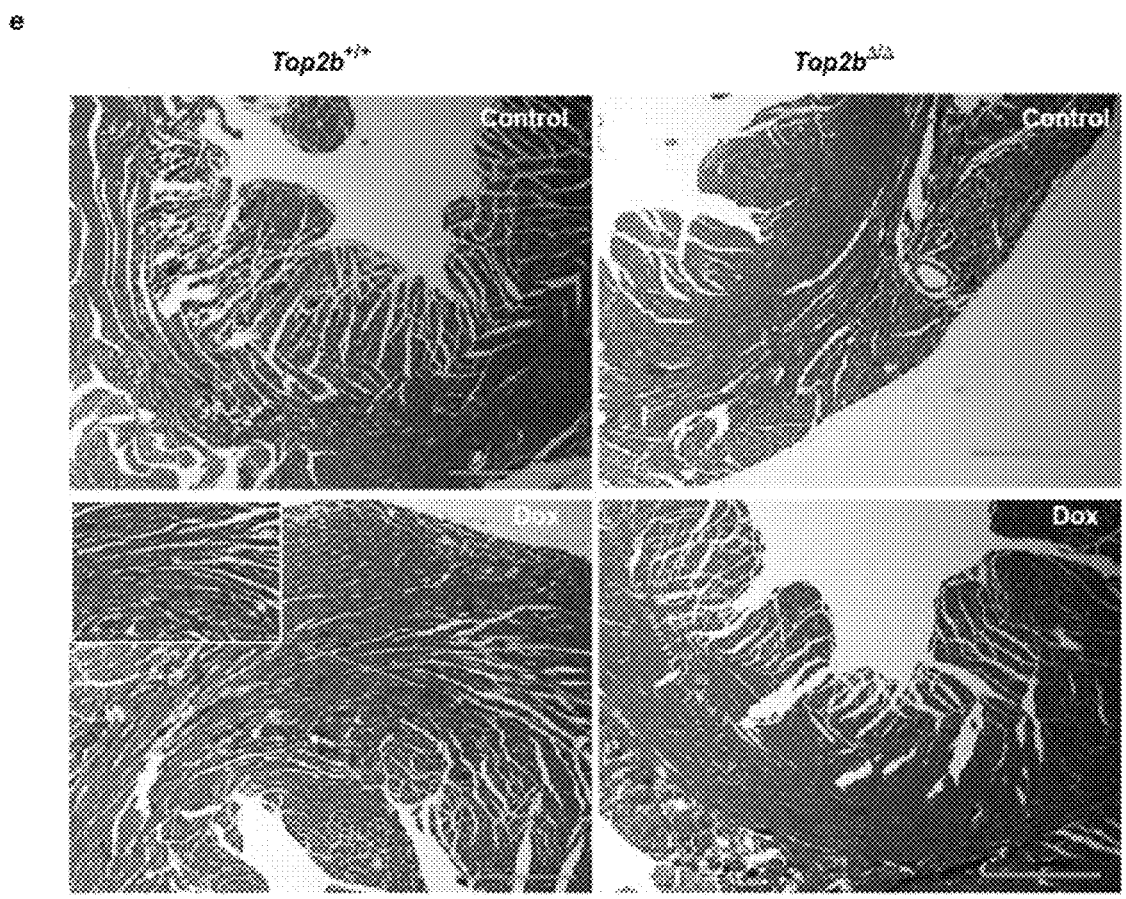

To establish the clinical relevance of the Top2b animal model, studies were undertaken to determine the effect of chronic administration of doxorubicin on left ventricular ejection fraction as measured by cardiac MRI (Wang, J. et al., 2010). Before Cre induction, cardiac MRI scan was performed on each mouse to examine the baseline ejection fraction. Cardiomyocyte-specific Cre induction was carried out by treating mice with tamoxifen. Two weeks after the last dose of tamoxifen, another cardiac MRI scan was performed to confirm that cardiac function was not affected by tamoxifen treatment. Doxorubicin treatment (5 mg/kg, i.p., once a week for 5 weeks) was started 7 days after the second MRI scan. Two weeks after the last dose of doxorubicin, a third MRI scan was performed (FIG. 6a).

Both end systolic and end diastolic volumes determined by cardiac MRI were markedly increased in the Top2b$^{+/+}$, Top2b$^{+/\Delta}$, but not in Top2b$^{\Delta/\Delta}$ mice after chronic doxorubicin exposure (FIGS. 2c, d). The base line ejection fractions were 53% in the Top2b$^{+/+}$, Top2b$^{+/\Delta}$, and Top2b$^{\Delta/\Delta}$ mice, respectively (FIG. 2e). Tamoxifen treatment did not significantly affect the ejection fractions in all three groups, suggesting that Top2b is not required for normal function of adult hearts. Following 5 weeks of doxorubicin treatment, the ejection fractions from the Top2b$^{+/+}$ and Top2b$^{+/\Delta}$ mice decreased from 53% to 43%, whereas the Top2b$^{\Delta/\Delta}$ mice had no change in the ejection fraction. These results revealed that Top2b is critical for doxorubicin to induce a reduction in ejection fraction, a clinical hallmark of doxorubicin-induced cardiomyopathy.

Tissues were also studies following 5 weeks of doxorubicin treatment. Reduction of genes involved in mitochondrial biogenesis, generation of ROS, ultrastructural changes in mitochondria, and increase in fibrosis were observed in doxorubicin-treated Top2b$^{+/+}$, but much less so in doxorubicin-treated Top2b$^{\Delta/\Delta}$ hearts (FIGS. 6b-e). Thus, similar pathology was observed in both the acute and chronic model and the pathological changes were all dependent on Top2b.

Figure 7E:
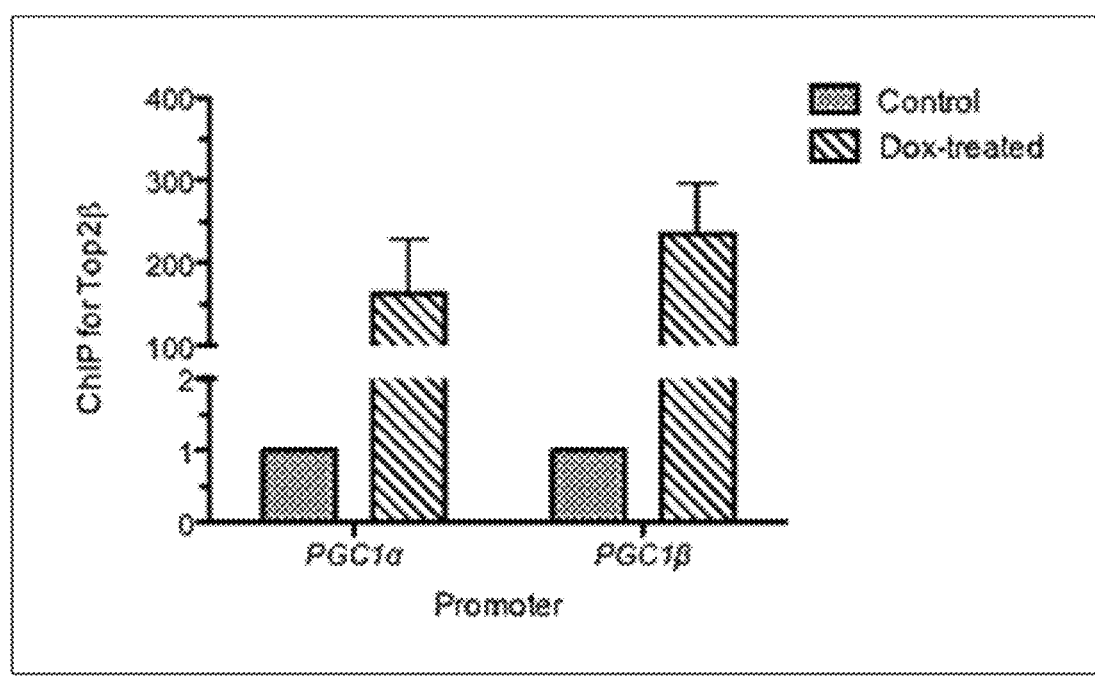

These results suggested that doxorubicin-induced cardiotoxicity is not simply due to redox cycling of doxorubicin alone. Specifically, Top2b was implicated as an essential driver of doxorubicin-induced cardiotoxicity. In the presence of Top2b, doxorubicin activated the DNA response and apoptosis pathways and triggered a marked alteration in the transcriptome that selectively affected oxidative phosphorylation and mitochondrial biogenesis in cardiomyocytes. These results also provided an alternative explanation for the classical observation that doxorubicin causes both structural and functional mitochondrial abnormalities (Wallace, K. B. 2003). This could be due to down regulation of both PGC-1α and PGC-1β, which are critical for mitochondrial biogenesis and function. Since inhibition/poisoning of Top2b by Top2-directed anticancer drugs (e.g. doxorubicin) leads to activation of DNA damage response, it is possible that DNA damage responses activated p53 to suppress PGC-1 transcription leading to defective mitochondria biogenesis and metabolic failure (Sahin, E. et al., 2011). It is also possible that doxorubicin-mediated inhibition/poisoning of Top2b could suppress transcription in a p53-independent manner. Top2β has been shown to be recruited to hormone promoters to regulate transcription (Ju, B. G. et al., 2006). Indeed, it was found that Top2b in the presence of doxorubicin binds avidly to the promoter of the PGC-1α and PGC-1β genes in both HL-1 cells and isolated cardiomyocytes (FIG. 7). The binding of the Top2b/doxorubicin complex to the promoters of PGC-1 is likely to be responsible for blocking transcription. However, formal proof of this mechanism would require additional studies. Taken together, Top2b is clearly the driver gene that is required to initiate the entire cardiotoxicity cascade.

The implications of these findings are two folds. First, drugs that specifically target the Top2a isozyme, but not Top2b, should have less cardiotoxicity and hence be more useful clinically. This is based on the assumption that Top2b does not contribute significantly to doxorubicin's tumoricidal activity. Second, patients with higher expression of Top2b should be more susceptible to doxorubicin-induced cardiotoxicity. These predictions were then further tested in human subjects.

Example 2

Materials and Methods for Example 1

Animals:

The use of animals, including all treatment was approved by Institutional Animal Care and Use Committees of the University of Texas-M.D. Anderson Cancer Center.

Generation of MHC-Cre Top2b$^{flox/flox}$ Mice:

The floxed Top2b mouse line was previously generated (Lyu, Y. L. et al., 2003). The Top2b$^{flox}$ allele contains two loxP sites flanking three Top2b exons that encode a region of Top2b containing the active-site tyrosyl residue; this allele expresses wild-type Top2b, but is converted to a null allele Top2b$^\Delta$ upon exposure to Cre recombinase. The Top2β$^{flox/flox}$ mice are viable and show normal growth and behavioral phenotypes. Cardiomyocyte-specific deletion within the floxed Top2b allele was achieved by crossing the Top2b$^{\Delta/\Delta}$ line with a mouse line purchased from Jackson Labs (Stock No. 005650). The mouse line carried an α-MHC promoter-driven Cre recombinase gene flanked on each end with a mutated murine estrogen receptor ligand binding domain (MerCreMer), thus Cre expression was tamoxifen-inducible yet estrogen insensitive and could be temporally controlled. First, Top2b$^{flox/flox}$ mice were crossed with mice carrying a α-MHC promoter-driven Cre recombinase (MHC-Cre), which produced progenies with the genotype of MHC-Cre Top2b$^{+/flox}$. Then the MHC-Cre Top2b$^{+/flox}$ mice were crossed with the Top2b$^{flox/flox}$ mice to generate the MHC-Cre Top2b$^{flox/flox}$ mice. Mice with the genotype of MHC-Cre Top2b$^{+/+}$ and MHC-Cre Top2b$^{+/flox}$ were generated as controls. Specific primers provided by the vender (Jackson Labs) were used to identify the Cre alleles. For the identification of the wild type Top2b (~820 bp) and the floxed Top2b (~600 bp) alleles, primers UpBglII (5'-ATATGGTACAGCAACAAAG-CATTTGACATA-3'; SEQ ID NO: 1) and PacIR (5'-TCAT-TGGGAGGCCAGAGCATC-3'; SEQ ID NO: 2) were used in PCR-based genotyping.

Deletion of Top2b in the Cardiomyocytes:

Four-week old mice were genotyped and those with genotypes of MHC-Cre Top2b$^{flox/flox}$, MHC-Cre Top2b$^{+/flox}$, and MHC-Cre Top2b$^{+/+}$ were treated with tamoxifen (25 mg/kg, once a day for 5 days) by gavage. Three genotypes of Top2b in the cardiomyocytes were generated, i.e. Top2b$^{+/+}$, Top2b$^{+/\Delta}$, and Top2b$^{\Delta/\Delta}$. These mice were used in all experiments. Effective deletion of Top2b in the cardiomyocytes was confirmed at the end of the experiments by reduced expression of Top2b in the cardiomyocytes detected by immunofluorescence staining of the heart sections.

MRI for Measuring Cardiac Function:

Every mouse in the EF experiments received 3 MRI scans, i.e., a baseline scan, a second scan 2 weeks after the end of tamoxifen treatment, and a third scan 2 weeks after the last dose of doxorubicin. Methods of MRI scan were described previously (Wang, J. et al.). Mice were anesthetized with isoflurane (2.5% in 97.5% $O_2$), and scanned on a 7.0 T Biospec small animal scanner (Bruker Biospin Inc., Billerica, Mass.). Imaging gradients with 60 mm inner diameter (ID) were used with a 35 mm ID linear birdcage-style volume resonator. T1-weighted anatomic reference images were acquired using a three dimension (3D) fast low-angle shot (FLASH) gradient echo sequence. A retrospectively gated FLASH pulse sequence was used to acquire cardiac cine images with excellent contrast between bright blood and adjacent myocardium. To measure volumetric left ventricular ejection fraction (LVEF), at least 6 short axis images were scanned at 1 mm interval from the apex to the base of the heart. End-diastolic (ED) and end-systolic (ES) left ventricular volumes were obtained by the biplane area length method, and LVEF was calculated with the equation: [(ED-ES)/ED]/100.

Doxorubicin Treatment:

Two weeks after completion of tamoxifen treatment mice were treated with doxorubicin or drug vehicle. Two cohorts of mice were treated with different schedules. For acute experiment to examine doxorubicin's effect on the hearts, mice were injected with doxorubicin (5 mg/kg or 25 mg/kg, ip) once, and hearts were removed for testing 16 h or 72 h after doxorubicin injection. To evaluate the chronic effect of doxorubicin on cardiac function, doxorubicin (5 mg/kg, i.p.) was administered once a week for 5 weeks, and cardiac function was examined 2 weeks after the last dose of doxorubicin by using MRI.

Detection of DNA Double Strand Breaks (DSBs):

After mice were sacrificed, hearts were perfused with ice-cold PBS, quickly removed, embedded in OCT compound (Fisher Scientific), and snap-frozen in liquid nitrogen. The heart was sectioned to 5 μm-thick slices using a cryostat. Heart sections were stored at −80° C. until immunofluorescence staining was performed. Heart sections were rinsed with PBS at room temperature, fixed in BD Cytofix/Cytoperm solution (BD Biosciences) for 15 m, washed in PBS, and permeabilized in BD Perm/Wash solution for 30 m. Heart sections were first blocked with BSA (2 mg/ml) for 30 m, then incubated with an mouse monoclonal anti-γ-H2AX antibody conjugated with Alexa Fluor 555 (Clone N1-431, BD Biosciences) for 1 h. Nuclei were stained with DAPI (Sigma, 1 µg/ml PBS), and the slides were sealed for examination with an Olympus epifluorescence microscope (Model BX51). To quantify DSBs, the numbers of γ-H2AX-positive nuclei and the total nuclei were counted in 5 microscopic fields (400×) per section. For each mouse, five heart sections were counted to determine the percentage of γ-H2AX-positive nuclei.

Detection of Reactive Oxygen Species (ROS):

The hearts were perfused with ice-cold PBS and quickly removed. The hearts were embedded in OCT and snap-frozen in liquid nitrogen. Series of 5 µm-thick slices were sectioned from the heart immediately. Tissue sections were then stained with Dihydroethidium (DHE, Invitrogen) for 15 m, followed by staining with DAPI (1 µg/ml, Sigma). Tissue slides were sealed and examined with an Olympus epifluorescence microscope (Model BX51). The numbers of DHE-positive nuclei and the total nuclei were counted in 5 microscopic fields (400×) per section. Five heart sections from each mouse were counted to determine the percentage of the DHE-positive nuclei.

Detection of Apoptosis in Heart Sections:

Apoptosis was detected by using TUNEL assay on heart sections. Heart harvest, sectioning, and storage were described above. Heart sections were warmed to room temperature before the apoptotic nuclei were stained by using a commercially available kit (In Situ Cell Death Detection Kit, Cat. No. 12156792910, Roche Applied Science). The entire staining procedures were performed according to the manufacturer's instructions. The nuclei were stained with DAPI (Sigma) before the slides were sealed and examined with an Olympus epifluorescence microscope (Model BX51). The apoptotic nuclei and the total nuclei per heart section were counted at 200× magnification. The apoptotic nuclei in 5 heart sections of each mouse were counted and averaged.

Transmission Electron Microscopy:

To examine doxorubicin-induced ultra-structural damages, wildtype and mice with Top2 deletion in the cardiomyocytes were treated with doxorubicin (25 mg/kg for 72 h or 5 mg/kg once a week for 5 weeks) or drug vehicle. Heart was quickly removed. After rinse with PBS and blot dried, 10-20 pieces of tissue samples (1×2×2 mm) were taken from the myocardium of the left ventricle. Tissue samples were immediately fixed in 3% phosphate glutaraldehyde. Before sectioning, tissue samples were washed in 1M sodium phosphate buffer (pH 7.3), post fixed in 1% osmium tetroxide for 1 h and dehydrated through a series of graded alcohol. Then tissue samples were infiltrated with acetone and phlybed 812 plastic resin and embedded in plastic block molds with 100% polybed 812. One micron sections (thick sections) were cut on ultra microtome and placed on glass slides and stained with toluidine blue. Ultra thin sections (80 nm) were cut from sample blocks using a RMC MTXL Ultra Microtome and mounted on 100 mesh copper grids. Grids were stained with 2% uranyl acetate and Reynold's lead stain. 9 sections were analyzed from each animal heart. Grids were examined with a JEOL 1230 electron microscope and images were capture with an AMTV 600 imaging system.

Western Blot:

Expression of Top2b was examined in the hearts of mice. After sacrifice, the heart was quickly removed and homogenized immediately in lysis buffer. After homogenization, the lysate was sonicated at 4° C. and an aliquot was removed for protein concentration measurement. The lysate was stored at −80° C. for western blot analysis. 20 µg of lysate proteins were electrophoresed and transferred to PVDF membranes. Blots were blocked with 5% non-fat dry milk, and incubated overnight at 4° C. with anti-Top2b antibody (Abcam). To detect mitochondrial proteins, the mitochondria were isolated from cardiomyocytes. The cardiomyocytes were isolated with a Langendorff perfusion system according to a published protocol3. Briefly, heart was removed and rinsed with ice-cold PBS twice before connecting to a Langendorff apparatus through the aorta. The heart was perfused first with perfusion buffer for 3 m at 37° C. (3 ml/min), then digestion buffer (enzyme-containing) buffer at 37° C. for 8-10 m. The heart was disintegrated manually and the tissue/cells were separated by using forceps. The tissue/cell suspension was incubated for another 3-5 m in digestion buffer, then triturate the cells gently using a 1 ml pipette before adding stopping buffer. After purification by centrifugation the mitochondria were isolated from the cardiomyocytes with a kit (Cat. No. MS853, Mitosciences) for separating mitochondria from nuclei and cytosol. The isolated mitochondria were homogenized in lysis buffer and sonicated before being stored at −80° C. until use. 20 µg of lysate proteins were electrophoresed and transferred to PVDF membranes. Blots were blocked incubated overnight at 4° C. with anti-Ndufa3 (Sigma), anti-Atp5a (Abcam) or anti-Sdha antibodies (Abcam). After incubation with HRP-conjugated secondary antibodies for 40 m at room temperature, the blots were detected with a luminol-based detection kit (ECL, GE Health Care).

Mitochondrial Membrane Potential Assay:

Mitochondria membrane potential was evaluated with JC-1 according to the manufacturer's protocol (Cat. No. 551302, BD Biosciences). JC-1 (5,5',6,6'-tetrachloro-1,1',3,3'-tetraethylbenzimidazolcarbocyanine iodide) is a lipophilic fluorochrome that is used to evaluate the status of the mitochondria membrane potential. JC-1 aggregates or monomers had different emission spectra (red and green, respectively). Uptake of JC-1 into mitochondria is driven by the mitochondrial membrane potential. In normal healthy cells high concentration of aggregates emit red fluorescence. Wildtype mice and mice with Top2b deletion in the cardiomyocytes were treated with doxorubicin (25 mg/kg, i.p.) 72 h before the heart was quickly removed for cardiomyocyte isolation as described above. The isolated cardiomyocytes were plated on a 35 mm petridish coated with gelatin and immediately stained with JC-1. The stained cells were examined by using an Olympus epifluorescence microscope.

Gene Expression Profiling:

Total RNA was extracted from cardiomyocytes isolated from mouse heart 16 or 72 h after treatment with doxorubicin (25 mg/kg) or drug vehicle using TRIZOL reagent (Invitrogen), then purified with RNeasy Mini Kit (Qiagen) according to the manufacturer's instructions. Purified RNA samples were shipped on dry ice to Miltenyi Biotec Inc. for microarray analysis. Quality control of the sample RNA was performed by the company. Before hybridization, 100 ng of each sample RNA was used for T7-based amplification and Cy3 labeling. The hybridization procedure was performed according to the Agilent 60-mer oligo microarray processing protocol using the Agilent Gene Expression Hybridization Kit (Agilent Technologies). After an overnight hybridization (65° C.) the microarrays were washed and scanned using Agilent Microarray Scanner System (Agilent Technologies). The microarray image files were processed using the Agilent Feature Extraction Software (FES). The software determined feature intensities and subtracted background, rejected outliers and calculated statistical confidences. To determine differential gene expression the FES derived output data files were further analyzed using the Rosetta Resolver® gene expression data analysis system (Rosetta Biosoftware). For network analysis using Ingenuity Pathway Analysis (IPA) software, the normalized experiment raw data from the company were exported to Microsoft Excel spreadsheets and rearranged to be compatible for IPA analysis.

RTq-PCR Analysis:

Isolation of cardiomyocytes from mouse heart was carried out with Langendorff perfusion apparatus according to the standard protocol described above. Total RNA extraction was performed with TRIZOL Reagent (Invitrogen) and purification with RNeasy Mini Kit (QIAGEN) according the manufacturer's protocol. The concentration of RNA obtained was measured using a super-sensitive NanoDrop ND1000 spectrophotometer (Thermo Scientific). Reverse transcription reaction was performed by using the High Capacity RNA-to-cDNA Kit (Applied Biosystem). In brief, cDNA was generated from 1 µg of RNA by RT Enzyme Mix according to the manufacturer's instructions on a PCR thermocycler (S1000TM Thermal Cycler, BIO-RAD, USA). The resulting cDNA was diluted to a final concentration of 50 ng/µl for PCR amplification. Real time quantitative PCR was carried out by using a 7900HT Fast Real-Time PCR System (Applied Biosystems). Mouse TaqMan® Gene primers and probes (FAM, Applied Biosystem), were used in PCR amplification. Mouse GAPDH was used as internal control (VIC®/MGB Probe, Primer Limited, Applied Biosystem). The following TaqMan® Gene primers/probes were used Sdha (Mm01352366_m1), ATP5a1: (Mm00431960_m1), Ndufa3 (Mm01329704_g1), Ppargc1a (PGC-1α, Mm01208835_m1), Ppargc1b (PGC-1β, Mm00504720_m1), Esrra (EER, Mm00433143_m1), Trp53inp1 (Mm00458141_m1), Fas: (Mm00433237_m1), Apaf1 (Mm01223702_m1), Bax (Mm00432051_m1), Mdm2 (Mm01233136_m1), and GAPDH: Mouse GAPD (GAPDH) Endogenous Control (VIC®/MGB Probe, Primer Limited). Comparative analyses of each gene were performed using company-provided softwares, SDS2.4 and RQ Manager 1.2.1 (Applied Biosystems). All amplifications were carried out at least in duplicates. The mRNA expression levels of each gene were calculated by using the 2-ΔΔCt (comparative threshold cycle) method, as detailed by the manufacturer (Applied Biosystems).

Chromatin Immunoprecipitation:

HL-1 cells were treated with or without DOX (1 µM) for 2 h and subsequently evaluated using the ChIP protocol as previously published (24-26). For ChIP assay on isolated cardiomyocytes, mice were treated with doxorubicin (25 mg/kg, ip) or drug vehicle. Hearts were removed 16 h after treatment and cardiomyocytes were isolated using an enzyme perfusion system as described above. Cells from 4 mice in each treatment group were pooled. Crosslink was performed immediately after cell isolation by treating the cells with paraformaldehyde according to the recommendation of the manufacturer of the ChIP kit. After sonication, 400 µg of DNA from each treatment group was incubated overnight with 2 µg of the Top2b antibody (Abcam #ab58442) or IgG control (Upstate Biotechnology). The protein/DNA complex was processed according to manufacturer's instructions provided with the ChIP kit (Upstate Biotechnology). The input and eluted DNA was purified with a DNA Purification kit (MoBio) and subject to real-time PCR analysis. For each individual treatment sample, the eluted ChIP product was normalized to the Input product to rule out differences in total DNA quantities between control and Dox-treatment samples. Primers for the realtime PCR were generated based on previously reported primer sequences for human and/or rat PGC-1α and PGC-1β promoters; prior to use, the primer sequences were blasted against the mouse genome to ensure a similar target region on the mouse PGC22 1α or PGC-1β promoter, respectively. The amplicon for each primer set is represented on the illustration (FIGS. 7d,e). The primer sequences are as follows:

Mouse PGC-1α promoter
Set 1:
5'-TCATGGATGTGCTGGGTTAG-3'  (SEQ ID NO: 3) forward

5'-CAGATGGTTGCTTGCACTAGA-3' (SEQ ID NO: 4) reverse

Set 2:
5'-CCACGGAAAGAATCATGAGG-3'  (SEQ ID NO: 5) forward

5'-AACCGCCACATTTGTTTAGG-3'  (SEQ ID NO: 6) reverse

Set 3:
5'-TTCCTCTCTAAGCGTTACTTCACTG-3' (SEQ ID NO: 7) forward

5'-CTCTTTCAACTCCAATCCACTCTG-3' (SEQ ID NO: 8) reverse

Mouse PGC-1β promoter
Set 1:
5'-ATTCAGTAGCTGGTGCATAGCAGGTGCTCA-3' (SEQ ID NO: 9) forward 5'-GGCTCTGTCACTTAGTAGATCTGAAGTGGA-3' (SEQ ID NO: 10) reverse Set 2:
5'-GTGCCGGAACAAAAGGTAGT-3' (SEQ ID NO: 11) forward 5'-CCAGCACGCTTTTAAGGAAC-3' (SEQ ID NO: 12) reverse Set 3:
5'-AACCGTCCAGCCTTTTCAGT-3' (SEQ ID NO: 13) forward 5'-TCAGCCTCCCTTGTACCTTG-3' (SEQ ID NO: 14) reverse Statistical Analysis:

Student t test was used to compare means between 2 groups, and One-way ANOVA followed by multiple comparisons among means were used to determine significant differences among multiple groups.

Example 3

Determining Dox Cardiotoxicity in Humans

An IRB protocol (Lab10-0520) was prepared to enroll 137 patients with doxorubicin exposure >450 mg/m$^2$ and preserved EF (>50%) and another group with doxorubicin exposure <250 mg/m$^2$ and reduced EF (<40%). These two distinct groups of patients will allow studies to ascertain whether Top2β can be used as a predictor for doxorubicin-induced cardiotoxicity. A sample size of 274 patients exposed to doxorubicin (137 in each arm of high and low doxorubicin sensitivity) will be adequate to detect a 5% difference in Top2b expression between each group with 80% power. Significance is at the 0.05 level.

Inclusion Criteria:
1. Patients 18 years of age and older with no known history of heart disease who have received doxorubicin are eligible.
2. Must have a previous baseline measurement demonstrating a left ventricular EF of >50% and no indication of left ventricular dysfunction prior to doxorubicin exposure demonstrated by either echocardiography (Echo), multiple gated acquisition scan (MUGA) or cardiac catheterization.
3. Patients who with either a or b:
   a. Known doxorubicin exposure of 450 mg/m² (high dose) with an EF of >50%
   b. Known exposure of <200 mg/m² (low dose) with a decrease in EF of 10% or greater and <40% after exposure.

Exclusion Criteria:
1. Patients are unwilling to sign informed consent.
2. Pre-existing diagnosis of heart failure or cardiomyopathy prior to receiving doxorubicin.
3. Those patients with a transient decrease in EF or patients who were on heart failure therapy at baseline (prior to initial doxorubicin exposure).
4. Decrease in EF caused by sepsis.
5. History of coronary artery disease prior to doxorubicin exposure.

Patients with a diagnosis of cancer who have received doxorubicin will be approached and requested to sign the consent form at any time when seen by the Cardiology service. Enrollment will begin with those patients who fit the criteria for low dose exposure with subsequent development of a decrease in EF. These patients will consist of 137 consecutive patients identified with a decrease in EF from the Cardiology Clinic, Inpatient Service or Echo Lab.

Analysis of the age, gender, and cancer type of the low exposure group will be performed prior to further enrollment. This information will be used to identify potential candidates of similar age and gender who fit criteria for high dose doxorubicin exposure without a decrease in EF. Enrollment for this group will consist of 137 consecutive patients who fit criteria and consent to participate.

Patients will be asked to consent to the acquisition, processing and storage of their material for use in future research projects. Samples will be de-identified and assigned a unique number that is not associated with the patient's medical record number (MRN). The amount of blood obtained for research purposes will be 50 ml. All demographic information will protected using HIPPA guidelines. A portion of collected blood will be used for protein extraction described below, while another portion of blood will be used for DNA extraction by using an extraction kit (QIAamp DNA Blood Maxi Kit, Qiagen, Valencia, Calif.), according to the manufacturer's instructions. Protein and DNA extraction will be carried out immediately after blood collection.

Top2b Protein Analysis in Blood

According to the IRB protocol, 20 ml of blood is drawn from each patient. An aliquot of 800 μl of blood was processed for DNA extraction and the rest of the blood is used for ELISA.

Sample preparation:
1. Add RBC lysis buffer* (5× volume) to the whole blood.
2. Incubate at 37° C. for 5 mines
3. Centrifuge at 2500 RPM for 5 mines at 4° C.
4. Aspirate the supernatant and add 10 ml RBC lysis buffer to cells.
5. Count the cell density.
6. Centrifuge the cells at 2500 RPM for 5 mines.
7. Aspirate the supernatant and add protein lysis buffer** 0.5 ml/10⁷ cells, keep on ice for 30'.
8. Sonication the protein lysate 30 cycles (30" on and 30" off) at 4° C.

*1× Red Blood Cell (RBC) Lysis buffer was formulated as follows: to 800 μl dH₂O is added: 8.3 g ammonium chloride (NH₄Cl); 1.0 g potassium bicarbonate (KHCO₃); 1.8 ml of 5% EDTA. The buffer is filter sterilized through 0.2 um filter and brought to a final volume of 1000 ml with autoclaved dH₂O.

**Protein Lysis buffer for ELISA buffer was formulated as follows: 5 mM HEPES, 1.5 mM MgCl₂, 0.2 mM EDTA, 0.5 mM DTT, and 1% NP-40. A proteinase inhibitor cocktail (Sigma) was also added to protein lysis buffer before use (1:1,000 V/V).

Top2b Indirect ELISA:
Reagents:
Antigen Coating buffer: 1% paraformaldehyde in PBS.
Wash buffer: PBS+0.05% Tween 20
Blocking buffer: 1% (w/v) BSA in wash buffer
Standard diluent: 1% (w/v) BSA in wash buffer without Tween 20
Substrate: TMB (Cell Signaling)
Stop solution: 2M sulfuric acid ELISA Procedure:
Antigen Coating
1. Prepare the antigen solution at the appropriate concentrations in 1% paraformaldehyde in PBS.
2. Standard preparation: The concentration of the synthetic top2b peptide (113 amino acid at the C-terminal of the protein, Abnova) was 0.22 μg/μl. Dilute 2 μl (0.44 μg) of the stock solution in 250 μl of the coating buffer, then make serial dilution (1/2-1/256).
3. Make sample dilution: Dilute the external control (protein extracted from pooled human peripheral blood white cells) and patient samples starting at 1/4 (50 ml sample in 200 ml coating buffer) then 2× dilution to 1/64.
4. Pipette 50 μl/well of the above solution to each well of the microtiter plate.
5. Coating and dry plate by Incubate at 37° C. for overnight.
6. Wash three times with PBS-T.
7. Blocking with 1% BSA in PBS at room temperature for 1 hour.
8. Dilute the polyclonal primary antibody (ab15565 1:500) in 1% BSA in PBS.
9. Add 50 μl of the diluted antibody to each well. Incubate at room temperature for 1.5 hours.
10. Wash the wells as described in step 6.
11. Dilute the enzyme-conjugated secondary antibody (anti-rabbit IgG-HRP) (1:5000) in 1% BSA in PBS. Add 50 μl of this solution to each well.
12. Incubate at room temperature for 1 hour.
13. Wash 6 times with PBS-T.
14. During the last incubation and immediately before use, prepare the enzyme substrate or bring the pre-made liquid substrate to room temperature.
15. Add 50 μl of the freshly TMB substrate to each well.
16. Color should develop in positive wells after 2-10 minutes.
17. Stop reaction by add 50 μl STOP solution.
18. Absorbance may be read directly in a microplate reader (450 nm).

The different concentrations of the standard peptide, the external control, and the patient sample were plotted against the optical densities. The amount of top2b (ng) was determined by using linear regression based on the ODs of the standard and normalized with protein concentration (ng/μg protein).

Figure 8:
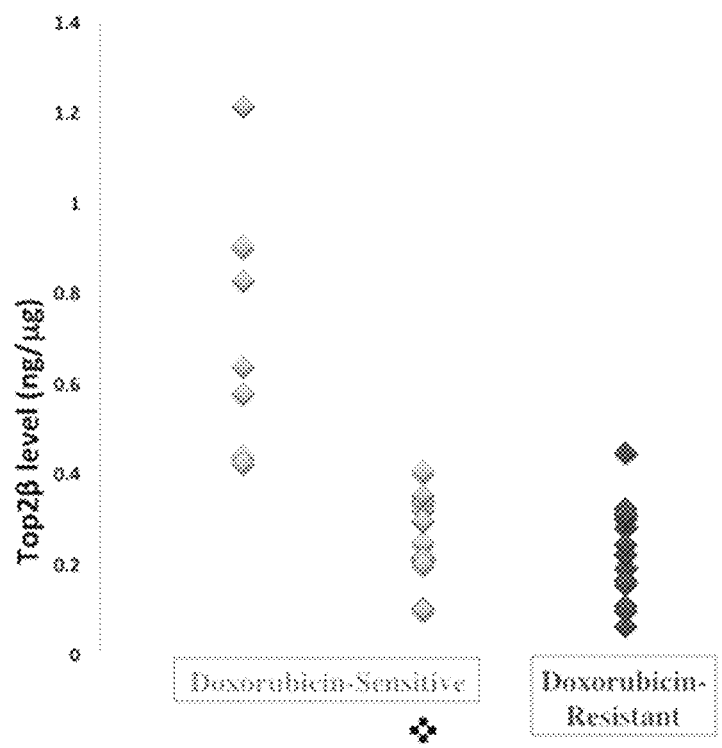
FIG. 8. Topoisomerase 2β expression in peripheral blood predicts susceptibility to anthracycline-induced cardiomyopathy. Graph shows the results obtained by measuring the level of Top2b protein expression in the peripheral blood of patients (y-axis). Plot shows the results for patients that were classed as Doxorubicin Sensitive or Doxorubicin Resistant with the Doxorubicin Sensitive group being further classified as having confounding factors (star below x-axis) or not having confounding factors. (see e.g., Example 3).

Initial results of these studies are shown in FIG. 8. The doxorubicin-sensitive group of patients was divided out between those with and without confounding factors, such as receiving Herceptin, having coronary artery disease, developing sepsis, and having hypertensive cardiomyopathy (FIG. 14). For this study, two groups of patients were enrolled, with 35 patients total. The anthracycline-sensitive group was defined as patients who received cumulative equivalent dose of doxorubicin <250 mg/m2 and had a decrease in ejection fraction (EF)≥10% from baseline and below 50% after exposure to doxorubicin. The anthracycline-resistant group was defined as patients who received cumulative equivalent dose of doxorubicin >450 mg/m2 and had preserved EF. Epirubicin and idarubicin were converted to the equivalent of doxorubicin dose using a conversion factor of 0.5 and 2, respectively. Patients who received dexrazoxane were excluded. Top2β levels in peripheral blood of patients were determined by enzyme-linked immunosorbent assay. There was no statistical difference between these two groups in terms of age, sex, and risk factors, such as hypertension, diabetes, dyslipidemia, and radiation exposure. All patients in the anthracycline-resistant group (n=15) had Top2β levels below a cut-point of 0.5 ng/μg. Top2β levels in the anthracycline-sensitive group (n=21) were significantly higher than the resistant group (0.4±0.28 vs. 0.23±0.1, p=0.026). Five anthracycline-sensitive patients had Top2β levels greater than 0.5 ng/μg. 14 anthracycline-sensitive patients with Top2b levels less than 0.5 ng/μg had confounding factors, such as CAD, sepsis, herceptin treatment, and hypertensive cardiomyopathy. Therefore, patients with Top2β levels above 0.5 ng/μg are at a higher risk for developing anthracycline-induced cardiotoxicity.

It is clear that there is a marked difference in the Top2b level in the peripheral blood between these two groups of patients. These preliminary results indicate that peripheral blood Top2b level can be used to predict patient's susceptibility to anthracycline-induced cardiotoxicity.

Example 4

Dexrazoxane Reduces Top2b Protein Levels in Heart Tissue

Figure 9:
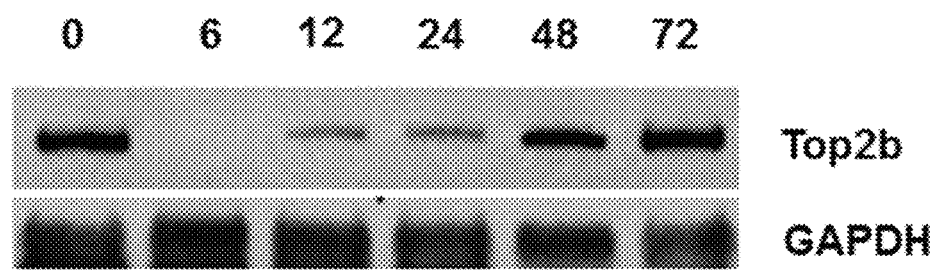
FIG. 9. The effect of dexrazoxane on Top2b protein levels. Mice were treated with dexrazoxane (100 mg/kg, i.p.) and heart tissue harvested after different time periods. Tissues were homogenized in lysis buffer, sonicated subject to western blotting to determine Top2b protein levels. GAPDH protein levels were assessed as a loading control.

To test the effect of dexrazoxane (Dex) on Top2b protein levels, mice were treated with dexrazoxane (100 mg/kg, i.p.). At different time points following treatment hearts were removed under anesthesia and perfused with PBS to remove blood. Each heart was cut into 10 pieces and snap-frozen in liquid nitrogen. Frozen tissues were homogenized in lysis buffer and sonicated to extract proteins for western blotting. As shown in FIG. 9, dexrazoxane administration greatly reduced Top2b protein levels in the heart, where Top2b was nearly undetectable at 6 hours after therapy. Top2b levels did not begin to recover until the 12 hour time point and were still noticeably reduced at 24 hours.

Figure 10:
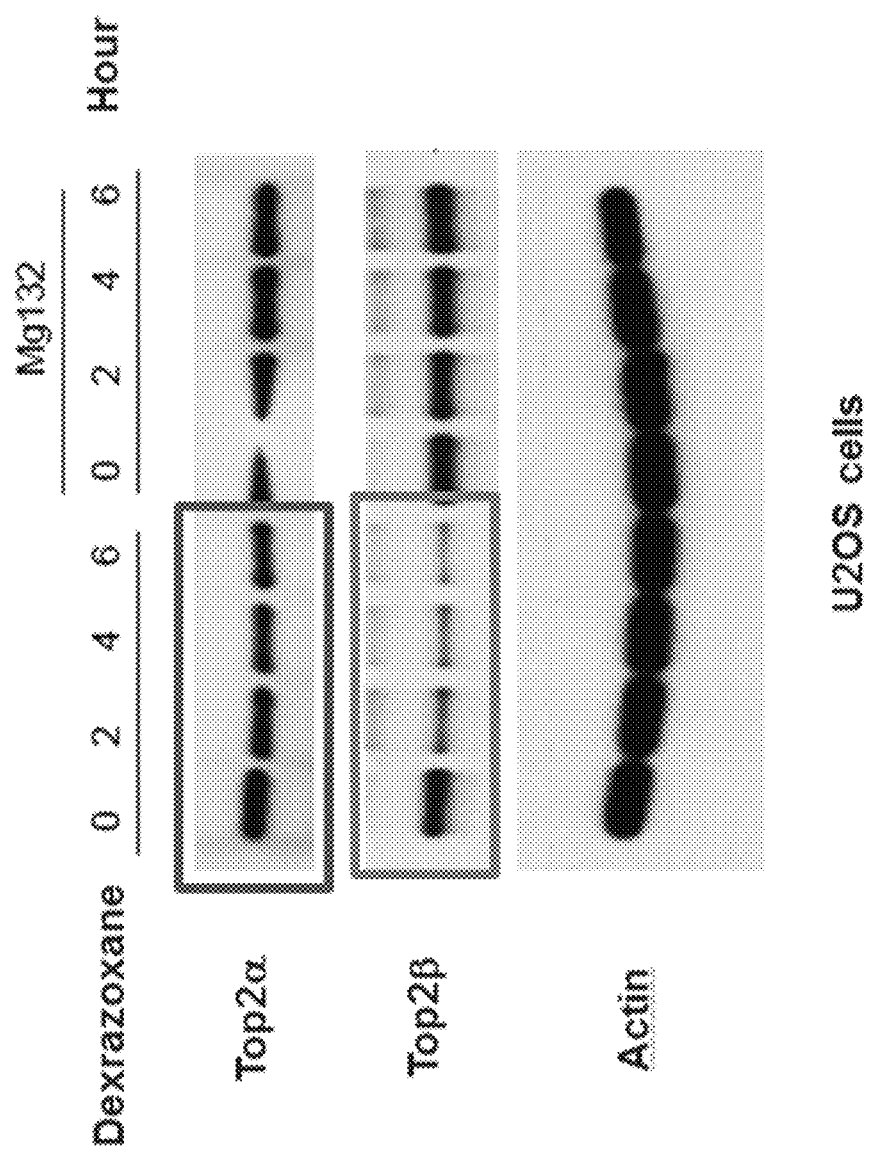
FIG. 10. Dexrazoxane caused degradation of Top2b, but not Top2a. U2OS cells were treated with 100 mM Dex and/or 10 mM MG132, a proteosome inhibitor, for 2, 4, or 6 hours. Cell lysates were immunoblotted with anti-Top2a, Top2b, or actin antibodies.

The effect of Dex treatment of Top2a levels was also tested. Briefly, U2OS cells were treated with 100 mM Dex and/or 10 mM MG132 (a proteosome inhibitor) for 2, 4, or 6 hours. Cell lysates were immunoblotted with anti-Top2a, Top2b, or actin antibodies. Results shown in FIG. 10 indicate that Rox caused degradation of Top2b, but not Top2a. Interestingly, Dex-mediated Top2b degradation was inhibited by MG132, suggesting a proteasome-dependent mechanism.

Figure 11:
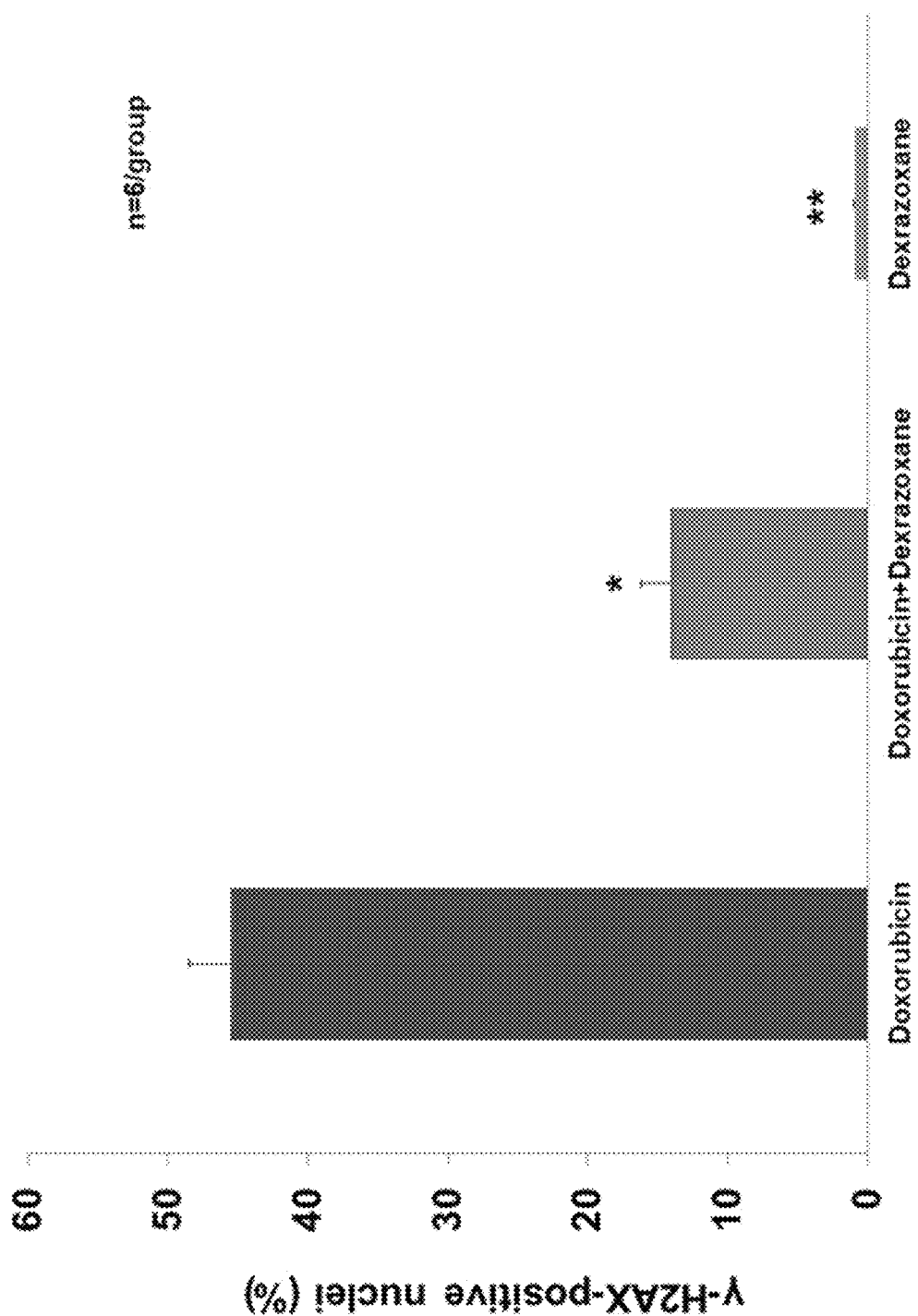
FIG. 11. Pre-treatment with dexrazoxane protects against doxorubicin-induced DNA double strand breaks in the heart. Dexrazoxane (100 mg/kg) was injected (ip) 8 hrs prior to doxorubicin (25 mg/kg) treatment. Hearts were harvested 16 hr after doxorubicin treatment. The percentage of γH2AX-positive nuclei was counted in 5 fields (400×) in each heart section. Five sections were counted in each heart to determine the average percentage of γH2AX-positive nuclei. One asterisk indicates a p value of 0.0000064, and 2 asterisks indicate a p value of 0.000000062.

To further confirm the cardio-protective effect of Dex, DNA double strand breaks were assessed in heart tissues. Dexrazoxane (100 mg/kg) was injected (ip) 8 hrs prior to doxorubicin (25 mg/kg) treatment. Hearts were harvested 16 hr after doxorubicin treatment. The percentage of γH2AX-positive nuclei was counted in 5 fields (400×) in each heart section. Five sections were counted in each heart to determine the average percentage of γH2AX-positive nuclei. Results are shown in FIG. 11 and demonstrate that pre-treatment with dexrazoxane protects against doxorubicin-induced DNA double strand breaks in the heart.

Figure 12:
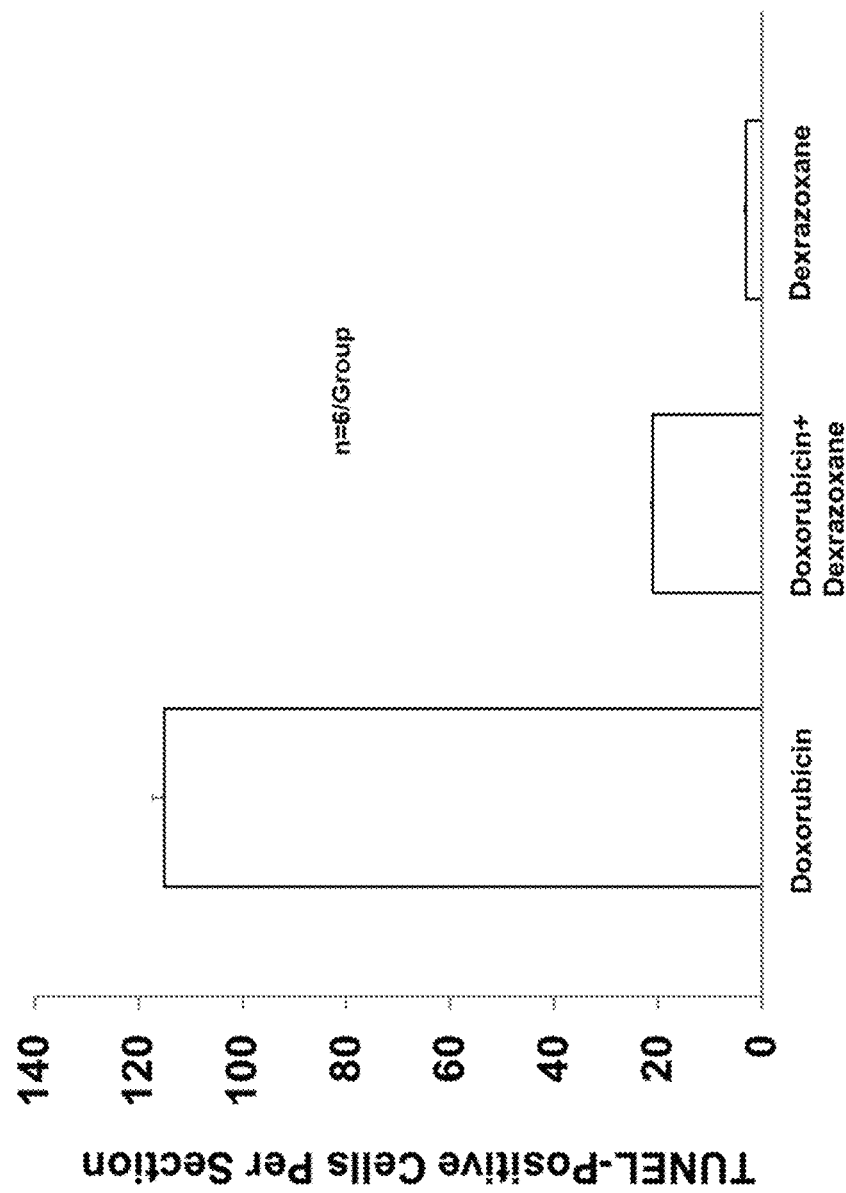
FIG. 12. Pre-treatment with dexrazoxane prevents doxorubicin-induced apoptosis in the mouse heart. Dexrazoxane (100 mg/kg) was injected (ip) 8 hrs prior to doxorubicin (15 mg/kg) injection (ip). One group received only doxorubicin and a second group received only dexrazoxane. Hearts were harvested 16 hrs after doxorubicin treatment. The number of TUNEL-positive nuclei were counted in five fields in each heart section.

The cardio-protective effect of Dex against doxirubin-induced apoptosis was assessed in heart tissues. Dexrazoxane (100 mg/kg) was injected (ip) 8 hrs prior to doxorubicin (25 mg/kg) injection (ip). One group received only doxorubicin and a second group received only dexrazoxane. Hearts were harvested 16 hrs after doxorubicin treatment. The numbers of TUNEL-positive nuclei were counted in five fields in each heart section. Results are shown in FIG. 12 and demonstrate that dexrazoxane pre-treatment protects against doxorubicin-induced apoptosis in the heart.

Figure 13:
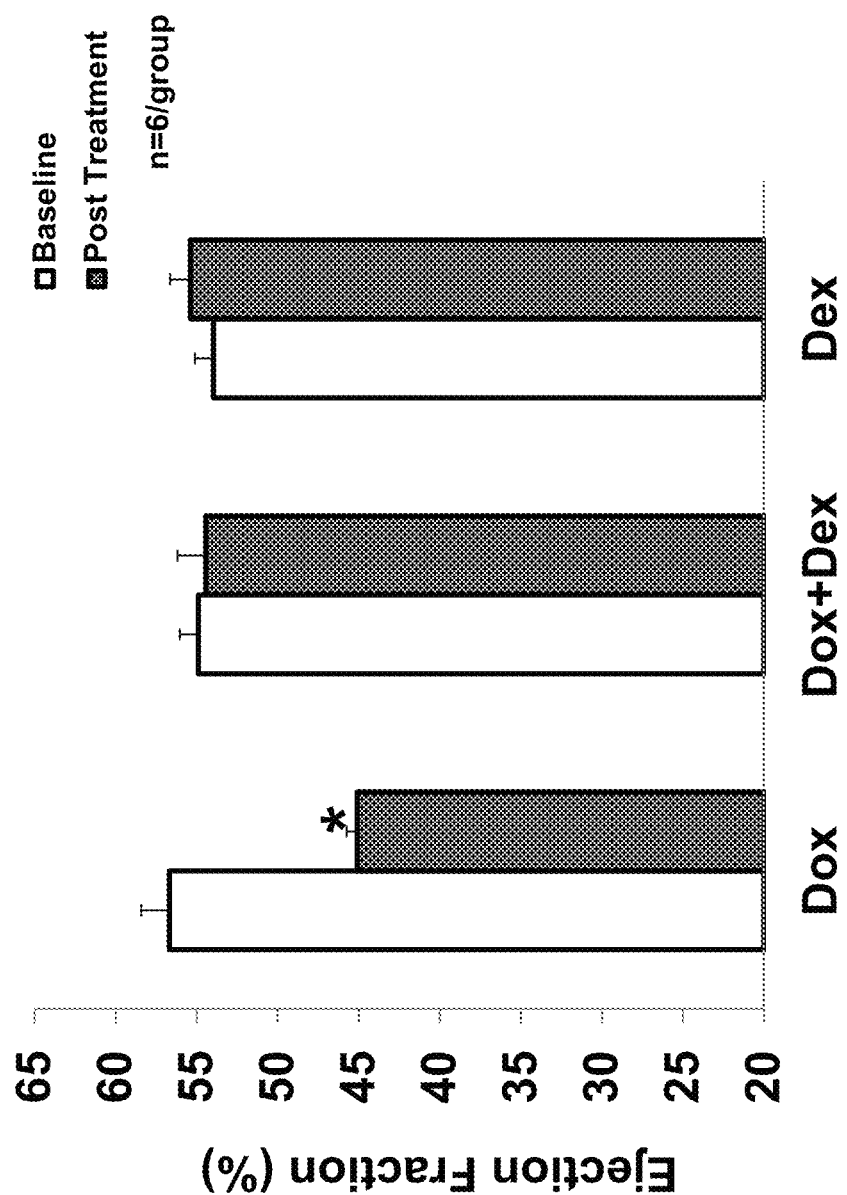
FIG. 13. Pre-treatment with dexrazoxane prevent doxorubicin-induced chronic heart failure in the mouse heart. Effect of chronic doxorubicin treatment (5 mg/kg, ip, once a week for 5 weeks) on ejection fraction. Dexrazoxane (100 mg/kg) was injected (ip) 8 hrs prior to doxorubicin. Bar represents mean±SEM and asterisks indicate significant difference ($p<0.01$).

The cardio-protective effect of dexrazoxane pre-treatment against doxorubicin-induced heart failure in the mouse heart. The effect of chronic doxorubicin treatment (5 mg/kg, ip, once a week for 5 weeks) was evaluated for its effect on ejection fraction. Following 5 weeks of doxorubicin treatment, the ejection fraction decreased from 57% to 45% (FIG. 13). The ejection fraction in mice treated with Dex either alone or in combination with doxorubicin treatment were unchanged. These results show that Dex pre-treatment is protective against heart failure induced by chronic doxorubicin treatment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Yeh, E. T. & Bickford, C. L. J Am Coll Cardiol 53, 2231-2247 (2009).
2. Force, T. & Kolaja, K. L. Nat Rev Drug Discov 10, 111-126 (2011).
3. Tewey, K. M., Rowe, T. C., Yang, L., Halligan, B. D. & Liu, L. F. Science 226, 466-468 (1984).
4. Capranico, G., Tinelli, S., Austin, C. A., Fisher, M. L. & Zunino, F. Biochim Biophys Acta 1132, 43-48 (1992).
5. Lyu, Y. L., et al. Mol Cell Biol 26, 7929-7941 (2006).
6. Singal, P. K. & Iliskovic, N. N Engl J Med 339, 900-905 (1998).
7. Myers, C., et al. Semin Oncol 10, 53-55 (1983).
8. Martin, E., et al. Toxicology 255, 72-79 (2009).
9. Lyu, Y. L., et al. Cancer Res 67, 8839-8846 (2007).
10. Lyu, Y. L. & Wang, J. C. Proc Natl Acad Sci USA 100, 7123-7128 (2003).
11. Sohal, D. S., et al. Circ Res 89, 20-25 (2001).
12. Okamura, S., et al. Mol Cell 8, 85-94 (2001).
13. Ogasawara, J., et al. Nature 364, 806-809 (1993).
14. Plesca, D., Mazumder, S. & Almasan, A. Methods Enzymol 446, 107-122 (2008).

15. Arany, Z., et al. Proc Natl Acad Sci USA 103, 10086-10091 (2006).
16. Lai, L., et al. Genes Dev 22, 1948-1961 (2008).
17. Wang, J., et al. Circ Res 106, 1904-1911 (2010).
18. Wallace, K. B. Pharmacol Toxicol 93, 105-115 (2003).
19. Sahin, E., et al. Nature 470, 359-365 (2011).
20. Ju, B. G., et al. Science 312, 1798-1802 (2006).
21. Lyu, Y. L. et al., Proc. Natl. Acad. Sci. U.S.A. 100, 7123-7128 (2003).
22. Wang, J. et al., Circ Res 106, 1904-1911.
23. Liao, R. et al., Methods Mol Med 139, 251-262 (2007).
24. Bawa-Khalfe, T., et al., J Biol Chem 282, 37341-37349 (2007).
25. Ishii, K. A. et al., Nat Med 15, 259-266 (2009).
26. Sahin, E. et al., Nature 470, 359-365 (2011).

What is claimed is:

1. A method for treating a subject having a cancer with an anthracycline therapeutic comprising: a) testing white blood cells of the subject's blood to determine a level of Top2b protein expression therein; b) comparing the level of Top2b protein expression determined in step a) to a reference; and (i) if the level of Top2b protein expression determined in step a) is lower than the reference, then administering an anthracycline therapeutic to the subject: or ii) if the level of Top2b protein expression in step a) is higher than the reference, then administering a cardioprotective agent to the subject.

2. The method of claim 1, wherein the cardioprotective agent is an agent that reduces Top2b protein levels in the subject.

3. The method of claim 2, wherein the agent that reduces Top2b protein levels comprises dexrazoxane.

4. The method of claim 1, wherein the cancer is a bladder cancer, breast cancer, lung cancer, stomach cancer, ovarian cancer, bladder cancer, Hodgkin's lymphoma, non-Hodgkin's lymphoma, cervical cancer, uterine cancer, prostate cancer, pancreatic cancer, adrenocortical cancer, liver cancer, Kaposi's sarcoma, Ewing's sarcoma, mesothelioma, multiple myeloma or a leukemia.

5. The method of claim 1, wherein the anthracycline therapeutic is comprised in a liposome.

6. The method of claim 1, wherein the anthracycline therapeutic is Daunorubicin, Doxorubicin, Epirubicin, Idarubicin, Valrubicin, or Mitoxantrone.

7. The method of claim 6, wherein the anthracycline therapeutic is doxorubicin.

8. The method of claim 1, further comprising administering an additional anticancer therapy to the subject.

9. The method of claim 8, wherein the additional anticancer therapy comprises radiation therapy, chemotherapy, immunotherapy or surgery.

10. The method of claim 1, further comprising in step ii) administering an anthracycline therapeutic.

11. The method of claim 1, wherein the reference is about 0.5 ng of Top2b protein for every μg protein extracted from pooled human peripheral blood white cells when determined by ELISA analysis.

12. The method of claim 1, wherein the protein level of Top2b is determined using an immunological assay.

13. The method of claim 1, wherein the level of Top2b expression determined in step a) is lower than the reference, and an anthracycline therapeutic is administered to the subject.

14. The method of claim 1, wherein the level of Top2b expression determined in step a) is higher than the reference, and a cardioprotective agent is administered in combination with an anthracycline therapeutic to the subject.

* * * * *